(12) United States Patent
McLuen

(10) Patent No.: US 8,187,332 B2
(45) Date of Patent: May 29, 2012

(54) BONE FUSION DEVICE

(75) Inventor: Gary R. McLuen, Port Townsend, WA (US)

(73) Assignee: McLuen Design, Inc., Port Townsend, WA (US)

( * ) Notice: Subject to any disclaimer, the term of this patent is extended or adjusted under 35 U.S.C. 154(b) by 571 days.

(21) Appl. No.: 11/484,379

(22) Filed: Jul. 10, 2006

(65) Prior Publication Data

US 2006/0253201 A1    Nov. 9, 2006

Related U.S. Application Data

(63) Continuation-in-part of application No. 11/357,319, filed on Feb. 16, 2006, now Pat. No. 7,727,280, which is a continuation-in-part of application No. 11/264,958, filed on Nov. 1, 2005, now abandoned.

(60) Provisional application No. 60/624,836, filed on Nov. 3, 2004.

(51) Int. Cl.
 *A61F 2/44* (2006.01)
(52) U.S. Cl. .................................................. 623/17.16
(58) Field of Classification Search .... 623/17.11–17.16, 623/16.11, 18.11; 606/62, 63, 60, 247–249
See application file for complete search history.

(56) References Cited

U.S. PATENT DOCUMENTS

| | | | |
|---|---|---|---|
| 4,961,740 A | 10/1990 | Ray et al. .......................... 606/61 |
| 5,015,247 A | 5/1991 | Michelson ....................... 606/61 |
| 5,443,514 A * | 8/1995 | Steffee ........................... 128/898 |
| 5,522,899 A * | 6/1996 | Michelson .................... 606/279 |
| 5,653,763 A | 8/1997 | Errico et al. | |
| 5,658,335 A * | 8/1997 | Allen .......................... 623/17.16 |
| 5,665,122 A | 9/1997 | Kambin | |
| 5,693,100 A | 12/1997 | Pisharodi | |
| 5,702,391 A | 12/1997 | Lin ................. 606/61 |
| 5,716,415 A * | 2/1998 | Steffee ......................... 623/17.16 |
| 5,800,547 A | 9/1998 | Schafer et al. .................. 623/17 |
| 5,800,550 A | 9/1998 | Sertich ............................. 623/17 |
| 5,885,287 A | 3/1999 | Bagby ............................. 606/61 |
| 6,045,579 A | 4/2000 | Hochshuler et al. ............ 623/17 |
| 6,080,158 A * | 6/2000 | Lin ............................. 623/17.16 |
| 6,080,193 A * | 6/2000 | Hochshuler et al. ....... 623/17.16 |
| 6,102,949 A | 8/2000 | Biedermann et al. ........... 623/17 |
| 6,102,950 A | 8/2000 | Vaccaro .......................... 623/17 |
| 6,176,882 B1 | 1/2001 | Biedermann et al. ...... 623/17.15 |
| 6,179,873 B1 | 1/2001 | Zientek ...................... 623/17.11 |
| 6,342,074 B1 | 1/2002 | Simpson .................... 623/17.11 |
| 6,371,968 B1 | 4/2002 | Kogasaka et al. ............. 606/190 |
| 6,371,987 B1 | 4/2002 | Weiland et al. ............ 623/17.11 |
| 6,375,655 B1* | 4/2002 | Zdeblick et al. ........... 623/17.16 |
| 6,409,766 B1 | 6/2002 | Brett .......................... 623/17.16 |

(Continued)

*Primary Examiner* — Alvin J Stewart
(74) *Attorney, Agent, or Firm* — Haverstock & Owens LLP

(57) ABSTRACT

A bone fusion device provides stability to bones during a bone fusion period. The bones include, for example, the vertebrae of a spinal column. The bone fusion device comprises one or more extendable tabs attached to the bone fusion device by associated rotating means. The bone fusion device is preferably inserted by using an arthroscopic surgical procedure. During arthroscopic insertion of the device, the tabs are pre-configured for compactness. In this compact configuration, the tabs are preferably deposed along and/or within an exterior surface of the bone fusion device. After the bone fusion device has been positioned between the bones, one or more tab(s) are extended. In the preferred embodiment, the position of each tab is related to a positioning element and extending blocks. Typically, the tabs advantageously position and brace the bone fusion device in the confined space between the bones until the bones have fused.

37 Claims, 18 Drawing Sheets

U.S. PATENT DOCUMENTS

| | | |
|---|---|---|
| 6,436,140 B1 | 8/2002 | Liu et al. ............... 623/17.11 |
| 6,464,727 B1 | 10/2002 | Sharkey et al. ........... 623/17.16 |
| 6,488,710 B2 | 12/2002 | Besselink ............... 623/17.15 |
| 6,491,695 B1 | 12/2002 | Roggenbuck .............. 606/61 |
| 6,527,803 B1 | 3/2003 | Crozet et al. |
| 6,562,041 B1 | 5/2003 | Yonemura et al. ........... 606/61 |
| 6,572,619 B2 | 6/2003 | Santilli ................. 606/61 |
| 6,576,016 B1 | 6/2003 | Hochshuler et al. ....... 623/17.15 |
| 6,582,431 B1 | 6/2003 | Ray .................. 606/61 |
| 6,582,467 B1 | 6/2003 | Teitelbaum et al. ....... 623/17.11 |
| 6,595,995 B2 | 7/2003 | Zdeblick et al. ............ 606/80 |
| 6,613,091 B1 | 9/2003 | Zdeblick et al. ........... 623/17.16 |
| 6,645,249 B2 | 11/2003 | Ralph et al. ............. 623/17.13 |
| 6,666,888 B1 | 12/2003 | Jackson ................. 623/17.11 |
| 6,685,742 B1 | 2/2004 | Jackson |
| 6,709,458 B2 | 3/2004 | Michelson |
| 6,746,454 B2 * | 6/2004 | Winterbottom et al. ........ 606/99 |
| 6,767,367 B1 | 7/2004 | Michelson ............... 623/17.16 |
| 6,770,096 B2 | 8/2004 | Bolger et al. ............ 623/17.16 |
| 6,821,298 B1 | 11/2004 | Jackson |
| 6,902,568 B2 | 6/2005 | Serhan |
| 6,923,830 B2 | 8/2005 | Michelson ............... 623/12.16 |
| 6,989,011 B2 | 1/2006 | Paul et al. |
| 7,018,415 B1 | 3/2006 | McKay .................. 623/17.15 |
| 7,128,760 B2 * | 10/2006 | Michelson ............... 623/17.15 |
| 7,166,130 B2 | 1/2007 | Ferre |
| 7,217,291 B2 * | 5/2007 | Zucherman et al. ....... 623/17.15 |
| 7,238,186 B2 * | 7/2007 | Zdeblick et al. .......... 623/17.16 |
| 7,331,996 B2 * | 2/2008 | Sato et al. .............. 623/17.16 |
| 7,479,160 B2 * | 1/2009 | Branch et al. ........... 623/17.11 |
| 7,621,956 B2 | 11/2009 | Paul et al. |
| 7,674,296 B2 | 3/2010 | Rhoda et al. |
| 7,727,280 B2 * | 6/2010 | McLuen ................. 623/17.16 |
| 7,758,617 B2 | 7/2010 | Iott et al. |
| D626,233 S * | 10/2010 | Cipoletti et al. ........... D24/155 |
| 7,811,327 B2 | 10/2010 | Hansell et al. |
| 7,837,688 B2 | 11/2010 | Boyer, II et al. |
| 7,837,734 B2 * | 11/2010 | Zucherman et al. ....... 623/17.15 |
| 8,062,375 B2 | 11/2011 | Glerum et al. |
| 2004/0127993 A1 * | 7/2004 | Kast et al. ................ 623/17.16 |
| 2005/0015149 A1 * | 1/2005 | Michelson ............... 623/17.11 |
| 2005/0283236 A1 | 12/2005 | Razian ................. 623/17.11 |
| 2006/0069436 A1 | 3/2006 | Sutton et al. |
| 2006/0241774 A1 | 10/2006 | Attali et al. |
| 2007/0093897 A1 * | 4/2007 | Gerbec et al. ............ 623/17.11 |
| 2008/0009880 A1 * | 1/2008 | Warnick et al. ............ 606/99 |
| 2008/0015701 A1 * | 1/2008 | Garcia et al. ............. 623/17.16 |
| 2008/0132949 A1 | 6/2008 | Aferzon et al. |
| 2008/0140207 A1 | 6/2008 | Olmos et al. |
| 2008/0288076 A1 * | 11/2008 | Soo et al. ............... 623/17.16 |
| 2009/0099601 A1 | 4/2009 | Aferzon et al. |
| 2009/0164020 A1 | 6/2009 | Janowski et al. |

* cited by examiner

BONE FUSION DEVICE

RELATED APPLICATIONS

This application is a continuation-in-part of U.S. patent application Ser. No. 11/357,319, filed on Feb. 16, 2006 now U.S. Pat. No. 7,727,280 and entitled "BONE FUSION DEVICE" which is hereby incorporated by reference, and which is a continuation-in-part of U.S. patent application Ser. No. 11/264,958, filed on Nov. 1, 2005 now abandoned and entitled "BONE FUSION DEVICE" which is hereby incorporated by reference, and which claims priority under 35 U.S.C. §119(e) of the co-pending U.S. Provisional Patent Application Ser. No. 60/624, 836, filed Nov. 3, 2004, and entitled "BONE FUSION DEVICE" which is hereby incorporated by reference.

FIELD OF THE INVENTION

This invention relates generally to bone fusion devices. More specifically, the present invention relates to devices for fusing vertebrae of the spine that can be inserted arthroscopically.

BACKGROUND OF THE INVENTION

The spinal column is made up of vertebrae stacked on top of one another. Between the vertebrae are discs which are gel-like cushions that act as shock-absorbers and keep the spine flexible. Injury, disease, or excessive pressure on the discs can cause degenerative disc disease or other disorders where the disc becomes thinner and allows the vertebrae to move closer together or become misaligned. As a result, nerves may become pinched, causing pain that radiates into other parts of the body, or instability of the vertebrae may ensue.

One method for correcting disc-related disorders is to insert a fusion cage between the vertebrae to act as a structural replacement for the deteriorated disc. The fusion cage is typically a hollow metal device usually made of titanium. Once inserted, the fusion cage maintains the proper separation between the vertebrae to prevent nerves from being pinched and provides structural stability to the spine. Also, the inside of the cage is filled with bone graft material which eventually fuses permanently with the adjacent vertebrae into a single unit.

The use of fusion cages for fusion and stabilization of vertebrae in the spine is known in the prior art. U.S. Pat. No. 4,961,740 to Ray, et al. entitled. "V-Thread Fusion Cage and Method of Fusing a Bone Joint," discloses a fusion cage with a threaded outer surface, where the crown of the thread is sharp and cuts into the bone. Perforations are provided in valleys between adjacent turns of the thread. The cage can be screwed into a threaded bore provided in the bone structure at the surgical site and then packed with bone chips which promote fusion.

U.S. Pat. No. 5,015,247 to Michelson entitled, "Threaded Spinal Implant," discloses a fusion implant comprising a cylindrical member having a series of threads on the exterior of the cylindrical member for engaging the vertebrae to maintain the implant in place and a plurality of openings in the cylindrical surface.

U.S. Pat. No. 6,342,074 to Simpson entitled, "Anterior Lumbar Underbody Fusion Implant and Method For Fusing Adjacent Vertebrae," discloses a one-piece spinal fusion implant comprising a hollow body having an access passage for insertion of bone graft material into the intervertebral space after the implant has been affixed to adjacent vertebrae. The implant provides a pair of screw-receiving passages that are oppositely inclined relative to a central plane. In one embodiment, the screw-receiving passages enable the head of an orthopaedic screw to be retained entirely within the access passage.

U.S. Pat. No. 5,885,287 to Bagby entitled, "Self-tapping Interbody Bone Implant," discloses a bone joining implant with a rigid, implantable base body having an outer surface with at least one bone bed engaging portion configured for engaging between a pair of bone bodies to be joined, wherein at least one spline is provided by the bone bed engaging portion, the spline being constructed and arranged to extend outwardly of the body and having an undercut portion.

U.S. Pat. No. 6,582,467 to Teitelbaum et al. entitled, "Expandable Fusion Cage," discloses an expandable fusion cage where the surfaces of the cage have multiple portions cut out of the metal to form sharp barbs. As the cage is expanded, the sharp barbs protrude into the subcortical bone of the vertebrae to secure the cage in place. The cage is filled with bone or bone matrix material.

U.S. Pat. No. 5,800,550 to Sertich entitled, "Interbody Fusion Cage," discloses a prosthetic device which includes an inert generally rectangularly shaped support body adapted to be seated on hard end plates of vertebrae. The support body has top and bottom faces. A first peg is movably mounted in a first aperture located in the support body, and the first aperture terminates at one of the top and bottom faces of the support body. Further, the first peg projects away from the one of the top and bottom faces and into an adjacent vertebra to secure the support body in place relative to the vertebra.

U.S. Pat. No. 6,436,140 to Liu et al. entitled, "Expandable Interbody Fusion Cage and Method for Insertion," discloses an expandable hollow interbody fusion device, wherein the body is divided into a number of branches connected to one another at a fixed end and separated at an expandable end. The expandable cage may be inserted in its substantially cylindrical form and may be expanded by movement of an expansion member to establish lordosis of the spine. An expansion member interacts with the interior surfaces of the device to maintain the cage in the expanded condition and provide a large internal chamber for receiving bone in-growth material.

These patents all disclose fusion cage devices that can be inserted between vertebrae of the spine in an invasive surgical procedure. Such an invasive surgical procedure requires a long recovery period.

SUMMARY OF THE INVENTION

The present invention is a bone fusion device for insertion between bones that are to be fused together, such as, for example, the vertebrae of a spinal column. The bone fusion device comprises one or more extendable tabs. The bone fusion device is in its most compact state when the tabs are aligned with the body of the device such that the tabs lie within the exterior of the device. In this compact form, the bone fusion device is preferably inserted between the vertebrae by using an arthroscopic procedure. The bone fusion device of some embodiments is filled with bone graft material. In these embodiments, the bone graft material is typically relocated from the interior to the exterior of the bone fusion device by using a lead screw. After the device has been positioned between the vertebrae, and the lead screw is inserted to optionally deliver the bone graft material, selected tabs are extended. Preferably, two tabs are extended upon rotating a rotating means wherein extending blocks travel up the screw pushing out the angled tabs as the extending blocks approach the ends of the bone fusion device. The position of each tab relative to the bone fusion device is adjustable depending upon the configuration of the associated rotating means. In this way, the tabs are advantageously positioned in the confined space between the vertebrae to help brace the device until the bone has fused. Further, the tabs of the bone fusion device provide a larger surface area to which the bones attach and fuse during a healing period.

According to an embodiment of the present invention, the body of the bone fusion device is a round cylinder with end faces. The bone fusion device has conduits or holes that allow the bone graft material within the device to flow to the exterior of the device where the material contacts and grafts to the vertebrae. The extendable tabs are arranged in various configurations on the exterior of the bone fusion device, including the end faces. Preferably, the bone fusion device is rectangular and the tabs are attached to the body of the device on more than one side to optimally brace the device from multiple directions between the adjacent vertebrae. Alternatively, the bone fusion device has a rectangular shape with end faces and extendable tabs attached to multiple exterior surfaces.

Optionally, the bone fusion device of some embodiments includes protrusions, threading, and/or sharp features on the exterior surface and/or the extendable tabs. These features are configured to engage the adjacent vertebrae to provide a tighter interface between the device and the vertebrae.

DETAILED DESCRIPTION

In the following description, numerous details and alternatives are set forth for purpose of explanation. However, one of ordinary skill in the art will realize that the invention can be practiced without the use of these specific details. For instance, the figures and description below often refer to the vertebral bones of a spinal column. However, one of ordinary skill in the art will recognize that some embodiments of the invention are practiced for the fusion of other bones, including broken bones and/or joints. In other instances, well-known structures and devices are shown in block diagram form in order not to obscure the description of the invention with unnecessary detail.

Figure 1:
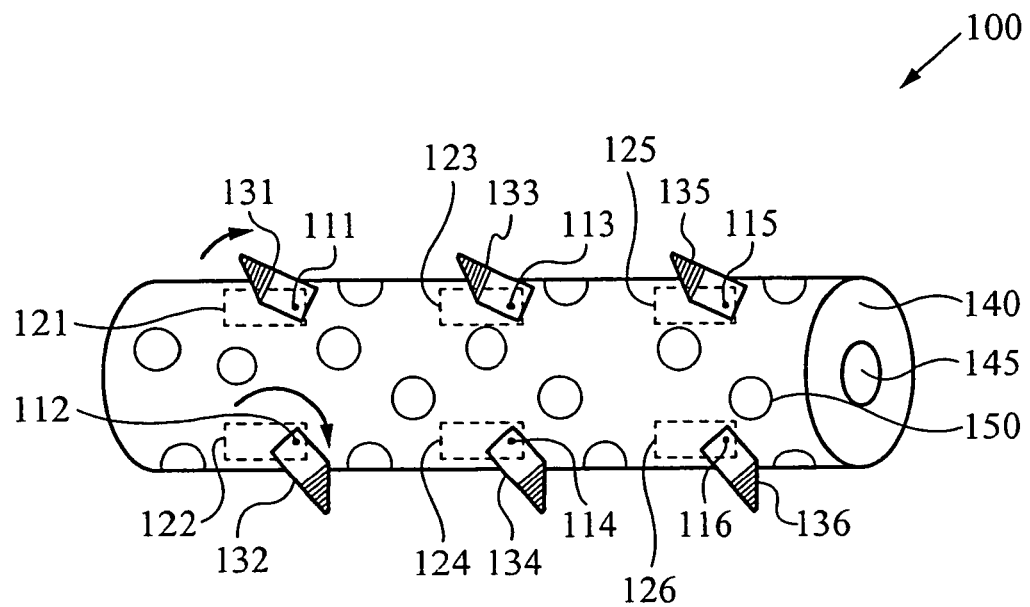
FIG. 1 illustrates a bone fusion device in accordance with some embodiments of the invention.

FIG. 1 illustrates a bone fusion device 100 in accordance with some embodiments of the invention. As shown in this figure, the bone fusion device 100 has a round cylindrical shape and has two end faces, including the end face 140. In some embodiments, the bone fusion device 100 is constructed from a high strength biocompatible material, such as titanium, which has the strength to withstand compressive and shear forces in the spine that are generated by a patient's body weight and daily movements. The base biocompatible material is often textured or coated with a porous material conducive to the growth of new bone cells on the bone fusion device 100.

Also shown in FIG. 1, the end face 140 has an opening 145 which allows the insertion of bone graft material into the bone fusion device 100. The bone graft material includes bone chips from the same patient (autograft), bone chips from a donor (allograft or xenograft), and/or a synthetic bone matrix. The bone graft material typically promotes bone growth during a recovery period after the patient receives bone fusion surgery. As further illustrated in FIG. 1, the bone fusion device 100 has several conduits or holes 150, which permit the bone graft material to contact the vertebral bone after the device 100 has been inserted between the vertebrae of the patient. The bone graft material and the surface texturing of the device 100 encourage the growth and fusion of bone from the neighboring vertebrae. The fusion and healing process will result in the bone fusion device 100 becoming embedded within the two adjacent vertebrae of the spine which eventually fuse together during the healing period.

As further illustrated in FIG. 1, several tabs 131, 132, 133, 134, 135, and 136 are distributed along the round cylindrical body of the bone fusion device 100. These tabs 131-136 are each attached to the bone fusion device 100 by a respective rotating means 111, 112, 113, 114, 115, and 116. The rotating means 111-116 is typically a turn screw type assembly. When the bone fusion device 100 is inserted into the patient's body, the tabs 131-136 lie along the body of the device 100, as shown by the dotted outlines 121-126 of the tabs. Thus, the unextended tabs 121-126 of the bone fusion device 100 provide a compact assembly that is suitable for insertion into the patient's body through an arthroscopic surgical procedure. An arthroscopic procedure is considered minimally invasive and has certain advantages over more invasive conventional surgical procedures. In an arthroscopic procedure, a smaller surgical incision is employed as compared to the size of the incision required for conventional invasive surgery. Moreover, arthroscopic procedures minimize or eliminate the need for excessive retraction of a patient's tissues such as muscles and nerves, thereby minimizing trauma and injury to the muscles and nerves and further reducing the patient's recovery time.

After insertion of the device 100 into the space between the patient's vertebrae, the surgeon selectively extends particular tabs 131-136 by rotating each selected tab's respective rotating means 111-116. The more each rotating means 111-116 is rotated, the farther its respective tab 131-136 elevates and extends outward from its initial position 121-126 along the body of the device 100. Each tab's 131-136 position is individually adjustable so as to optimally brace the device 100 between the vertebrae. Due to the compressive forces commonly associated with spinal column vertebrae, some embodiments include a range of motion for each tab that is slightly greater than 90 degrees. It was particularly discovered during the reduction to practice of this aspect of the present invention, that the tabs of these embodiments are rotated to an angle that is slightly more than about 90 degrees with respect to the surface of the bone fusion device. The tabs extended in this configuration were found to be capable of withstanding the greatest amount of compressive force.

The tabs 131-136, when extended, abut tightly against the surfaces of the vertebrae that are immediately adjacent to the bone fusion device 100. In some embodiments, the tabs 131-136 have sharp protrusions along the length of the tab for engaging the adjacent vertebrae, while the tabs 131-136 of some embodiments have screw-type threads for screwing into and engaging the vertebrae. Optionally, the tabs of some embodiments have surface texturing to encourage and enhance the growth of new bone on the tabs 131-136. This surface texturing is often similar to the surface texturing used on the main body of the device 100. Regardless of their texturing and/or particular physical characteristics, the tabs 131-136 advantageously wedge the bone fusion device 100 in a fixed position between the vertebrae and provide a larger surface area with which the adjacent vertebrae fuses during the healing period. Moreover, bone growth material, such as protein, is typically applied to the tabs 131-136 to stimulate the regeneration of bone cells needed for bone fusion. The application of bone growth material is described further in relation to FIG. 4.

In an alternative embodiment of the invention, the tabs of the device 100 have sharp ridges or threads which bite into the adjacent vertebrae, further helping to brace the device between the vertebrae. It will be readily apparent to one skilled in the art that there are a number of variations for the body and the tabs 131-136 of the bone fusion device 100. For instance, the bone fusion device 100 employs different numbers and/or configurations of tabs in different embodiments. Hence, the tabs 131-136 depicted in FIG. 1 are merely exemplary. Moreover, the tabs 131-136 are located anywhere over the exterior surface of the bone fusion device 100, in a variety of orientations. Specifically, the tabs 131-136 are arranged such that when they are extended, the tabs 131-136 act to stabilize the bone fusion device 100 against the vertebrae from several points and directions. Typically, the tighter the bone fusion device 100 is wedged between the adjacent vertebrae by the tabs 131-136, the more stability the device 100 provides to the vertebrae and the spine of the patient. The tabs 131-136 of the embodiments described above are critical to insure that the device 100 is not dislodged, since movement of the device 100 could cause serious injury to the patient, and especially because the inserted device is situated near the patient's spinal cord.

Figure 2:
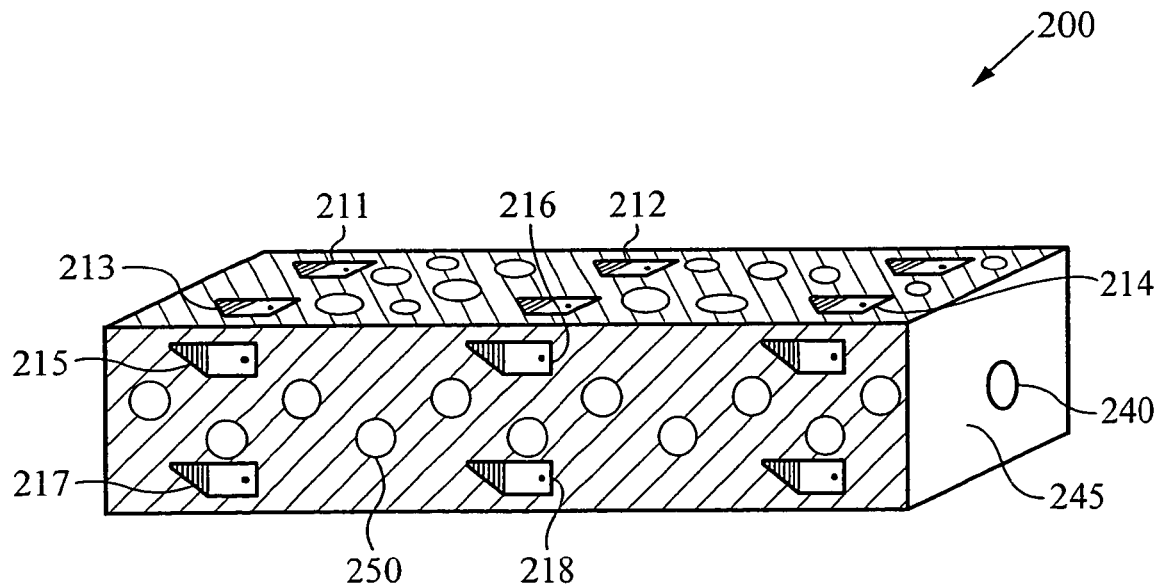
FIG. 2 illustrates a bone fusion device according to an alternative embodiment of the present invention.

FIG. 2 shows an alternative embodiment of the bone fusion device 200. As shown in this figure, the bone fusion device 200 of some embodiments has a rectangular shape. Similar to the round cylindrical shaped bone fusion device 100 shown in FIG. 1, the rectangular bone fusion device 200 has two end faces, including the end face 245 visible in FIG. 2, and multiple tabs 211, 212, 213, 214, 215, 216, 217, and 218 that are attached by rotating means to the exterior surface. The rotating means are screw type assemblies in some embodiments. The tabs 211-218 are also selectively extended after insertion of the bone fusion device 200 between the vertebrae. As before, the insertion of the bone fusion device 200 and the extension of the selected tabs 211-218, are typically performed by a surgeon during an arthroscopic surgical procedure. The procedure of some embodiments is further described in relation to FIG. 8. The rotation of a respective rotating means associated with each tab 211-218, individually adjusts the position of the associated tab 211-218 such that the device 200 is firmly braced between the two adjacent vertebrae. One skilled in the art will recognize that the tabs 211-218 are distributed over the exterior surfaces of the bone fusion device 200 in a variety of configurations, which include the ends and the surfaces of the device 200 that are not readily visible in FIG. 2. Moreover, as mentioned above, different numbers of tabs 211-218 are distributed over each surface of the bone fusion device 200 of different embodiments. In some embodiments, the surfaces of the bone fusion device 200 and/or the tabs 211-218, are coated with a porous surface texturing which promotes bone growth.

The end face 245 has an opening 240, which provides access to a cavity within the interior of the bone fusion device 200. In some embodiments, bone graft materials, such as the bone chips and/or the synthetic bone matrix that were mentioned above, are pre-loaded into the cavity within the bone fusion device 200 through the opening 240. Several conduits or holes 250 in the bone fusion device 200 permit the bone graft material to flow from the interior cavity to the exterior surfaces of the device 200 that are in contact with the vertebral bone. Typically, the bone graft material is relocated from the interior cavity to the exterior of the bone fusion device 200, after the device 200 has been positioned between the vertebrae. However, in some embodiments the bone graft material is delivered to the site of the bone fusion device 200 by arthroscopic means that originate external to the device 200. Regardless of the delivery means, the bone graft material and the surface texturing of the bone fusion device 200 encourage bone growth and fusion with the adjacent vertebrae that are in contact with the device 200. As bone fusion and healing progresses, the bone fusion device 200 becomes embedded within the two fused vertebrae of the spine.

Figure 3A:
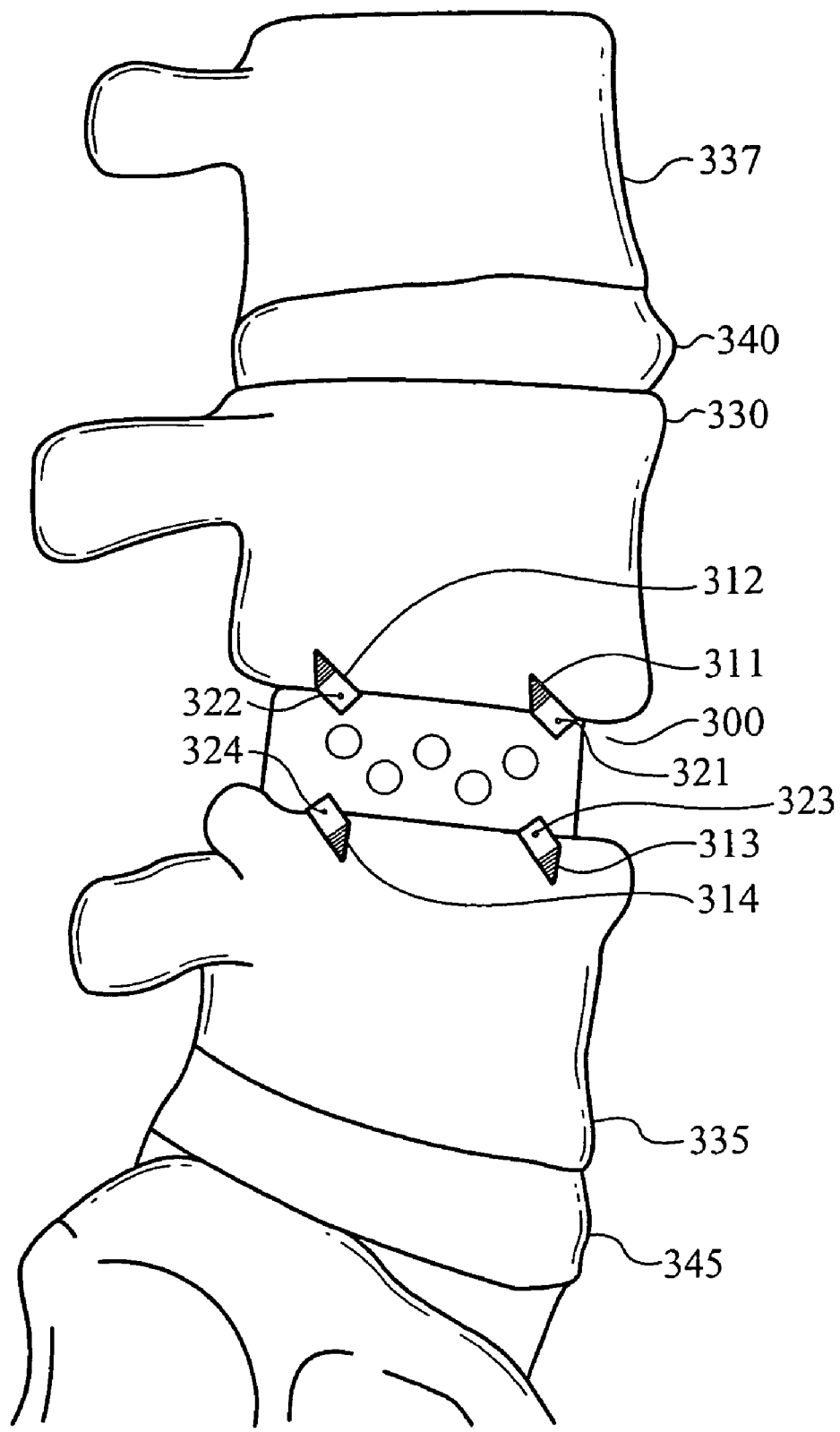
FIGS. 3A-B illustrate a section of a vertebral column showing the bone fusion device inserted between two adjacent vertebrae in place of an intervertebral disc.

FIG. 3A illustrates a section of a vertebral column that has a bone fusion device 300 positioned between two vertebrae 330 and 335. As shown in this figure, the bone fusion device 300 is positioned in a location where an intervertebral disc would normally reside. A flexible disc is typically sandwiched between the two vertebrae of a normal healthy spinal column. For instance, the normal, healthy disc 340 is sandwiched between the vertebrae 337 and 330. However, for the spinal column illustrated in FIG. 3, the intervertebral disc that normally resides between the vertebrae 330 and 335 has been excised and surgical insertion of the bone fusion device 300 has replaced the disc as the supporting structure between the vertebrae 330 and 335.

FIG. 3A further illustrates that the damaged disc that is normally sandwiched between vertebrae 330 and 335 has been totally removed. However, complete removal of the disc is not necessary in order to use the bone fusion device 300 of some embodiments. Typically, only as much of the disc needs to be excised as is required to permit the placement and positioning of the bone fusion device 300. Additionally, a sufficient amount of the disc is typically removed that allows access to the rotating means 311, 312, 313, and 314, which control the extension of the tabs 321, 322, 323, and 324, of the bone fusion device 300. As mentioned above, additional numbers and configurations of the tabs are distributed over the exterior surfaces of the bone fusion device 300, including the surfaces that are not visible in FIG. 3A.

During the insertion and placement of the bone fusion device 300, the tabs 321-324 are deposed in a position aligned along the body of the bone fusion device 300, such that the tabs 321-324 lie substantially within the exterior surfaces of the device 300. In some embodiments, the tabs 321-324 are flush with the exterior surface. In these embodiments, the form factor of the bone fusion device 300 is configured to be as compact as possible. For instance, the form factor of some embodiments has a diameter of approximately 0.28 inches and a length of approximately 1.0 inch. In contrast, the form factor of these same embodiments has a diameter of approximately 0.48 inches when the tabs 321-324 are fully extended.

By minimizing the space occupied, the bone fusion device 300 is advantageously inserted arthroscopically into the patient's body. If instead, the device 300 were inserted in its fully extended form, a larger surgical incision would be required, and a greater displacement of the muscles and nerves would be needed. However, its compact form factor allows the bone fusion device 300 to be inserted by advantageously utilizing minimally invasive arthroscopic techniques. Then, the tabs 321-324 of the bone fusion device 300 are extended after arthroscopic insertion to optimally increase the form factor and brace the device 300 between the vertebrae 330 and 335. In some embodiments, selected tabs 321-324 are extended.

Figure 3B:
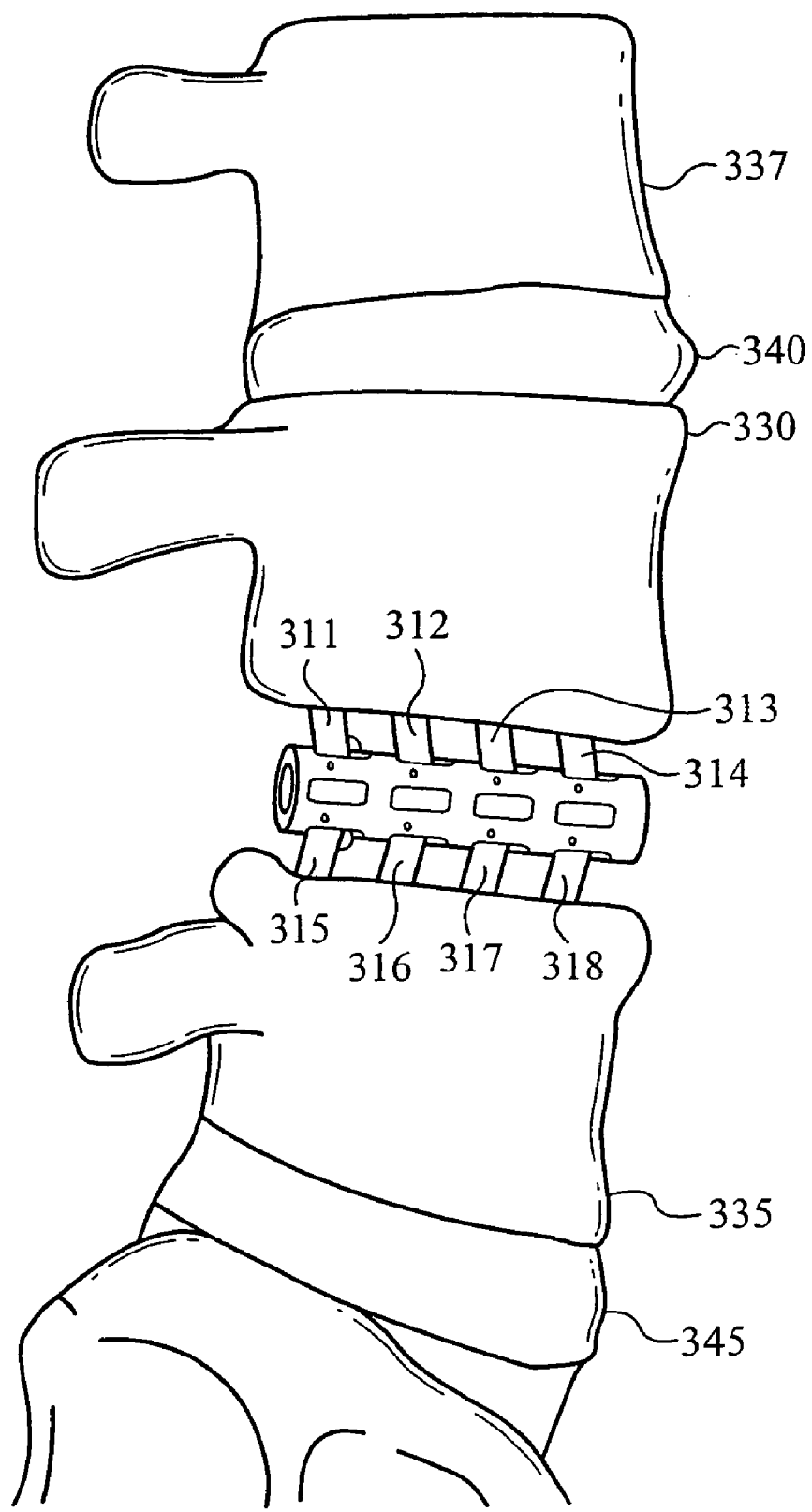

While the particular embodiment described above has a rectangular shape, it will be readily apparent to one skilled in the art that the cross-section of the bone fusion device 300 has different shapes in various embodiments. For instance, a more circular bone fusion device such as the device 100 illustrated in FIG. 1, or a device having another shape is employed in conjunction with a set of extendable tabs that are located in various configurations in additional embodiments of the invention. For instance, some embodiments have four rows of tabs, where each row is positioned on a side of the bone fusion device. In some of these embodiments, each row has four tabs. Such an embodiment is further described in relation to FIG. 7 and is illustrated in its inserted form in FIG. 3B. As shown in FIG. 3B, a first set of four tabs 311-314 lock the bone fusion device 300 against the vertebra 330, while a second set of tabs 315-318 lock the bone fusion device 300 against the vertebra 335.

Figure 4A:
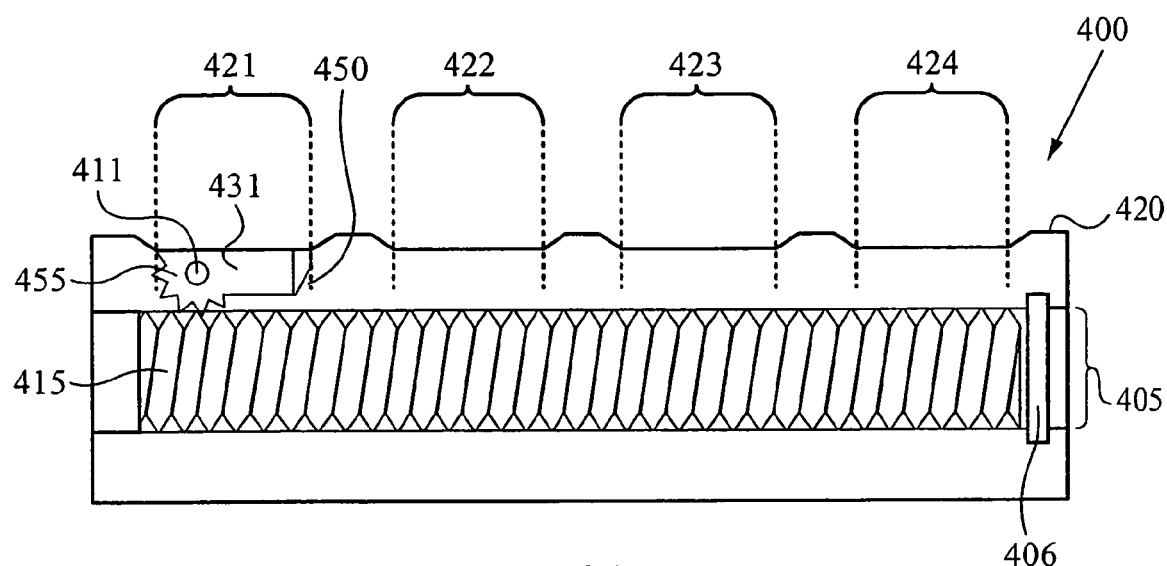
FIGS. 4A-B illustrate a detailed view of the worm screw drive and the extendable tabs of some embodiments.

FIG. 4A illustrates the bone fusion device 400 of some embodiments in further detail. As shown in this figure, the bone fusion device 400 includes an interior cavity 405 for the insertion of a lead screw 415, and one or more tabs 431 each deposed in a tab bay 421, 422, 423, 424.

The tab bays 421-424 allow the tabs 431 to lie flush and/or within the exterior surface 420 of the bone fusion device 400 when not extended. Also when not extended, the tab 431 and tab bay 421 provides a conduit 450 from the interior cavity 405 to the exterior surface 420 of the bone fusion device 400, such that the bone graft and/or growth material within the interior cavity 405 has a directed path to the exterior surface 420. Typically, the insertion of the lead screw 415 forces the material within the interior cavity 405 to relocate to the exterior surface 420.

The tab 431 includes a rotating means 411 and gear teeth 455. When the tab 431 is not extended, the gear teeth 455 provide a series of passive grooves by which the lead screw 415 traverses the interior cavity 405. Typically, the tab 431 remains fixed as the lead screw 415 is screwed into the interior cavity 405. In these embodiments, the threading of the lead screw 415 does not address or affect the gear teeth 455 during the insertion of the lead screw 415.

However, the gear teeth 455 do employ the threading of the lead screw 415 when the lead screw 415 has been fully inserted into the cavity 405, in some embodiments. For instance, in a particular implementation of the invention, the lead screw 415 is driven into the cavity 405, until it reaches an endcap 406. The endcap 406 allows the lead screw 415 to continue rotating in place, but does not allow the lead screw 415 to continue its forward progress through the cavity 405. When the lead screw 415 of these embodiments rotates without making forward progress, the rotating lead screw's threading contacts and engages the gear teeth 455 of each tab 431. Accordingly, the motion and angle of the spiraling threads, when applied against the gear teeth 455, causes the tabs 431 to elevate and extend. The combination of the gear teeth 455 on the tabs 431 and the inserted lead screw 415, is referred to, in some embodiments, as a worm screw drive mechanism.

In an alternative embodiment of the worm screw drive mechanism, the rotating means 411 is turned to raise the tab 431. In these embodiments, the rotating means 411 for the tab 431 typically comprises a turn screw type mechanism such that when the rotating means 411 is turned, the gear teeth 455 drive or rotate against the stationary threads of the inserted lead screw 415. Similarly, due to the angle of the stationary lead screw's spiral threads, the gear teeth 455 cause the tab 431 to elevate and extend above the exterior surface 420 of the bone fusion device 400.

Figure 4B:
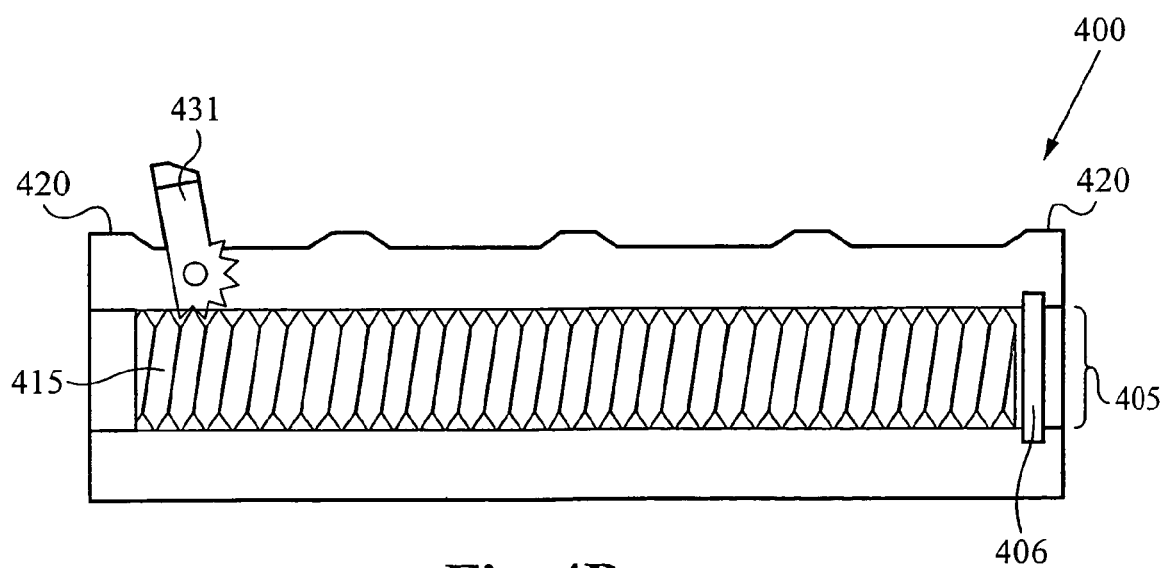

As mentioned above, the tabs 431 of some embodiments have a range of motion that exceeds 90 degrees with respect to the exterior surface 420 of the bone fusion device 400. Accordingly, FIG. 4B illustrates the tab 431 extended slightly past 90 degrees, which is the optimum position to withstand the compressive force exerted on the vertebrae of some embodiments.

Figure 5A:
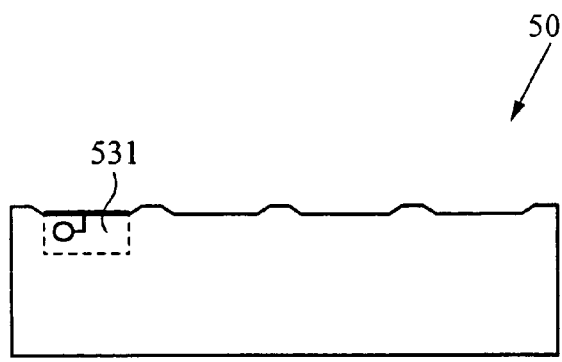
FIGS. 5A-B illustrate the small form factor of some embodiments.
Figure 5B:
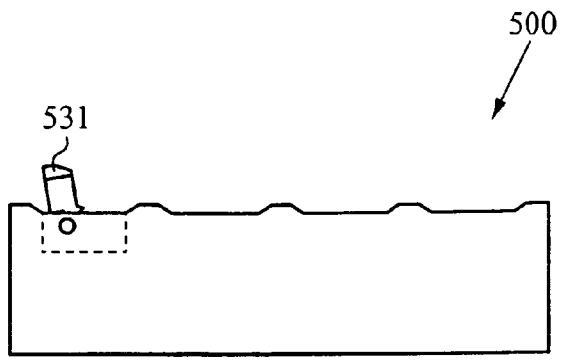
Figure 6A:
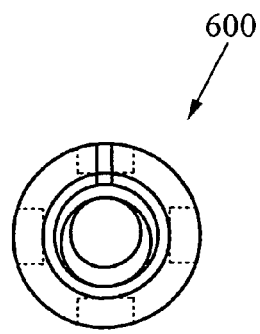
FIGS. 6A-B illustrate a cross section view of the small form factor of some embodiments.
Figure 6B:
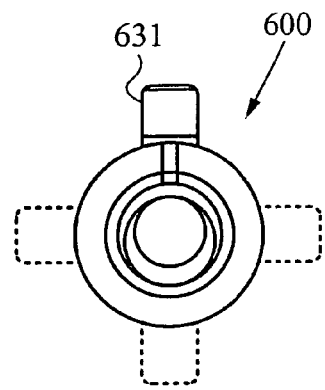

FIG. 5A illustrates a closed view of the small form factor for a bone fusion device 500 in accordance with some embodiments. As shown in this figure, the bone fusion device 500 has a tab 531 that is not extended and lies within the exterior surface of the device 500. In contrast, FIG. 5B illustrates the form factor for the bone fusion device 500 with the tab 531 extended, as described above. Similarly, FIG. 6A illustrates a cross section view of the bone fusion device 600 having a small form factor, while FIG. 6B illustrates the cross section view with the tab 631 extended.

Figure 7A:
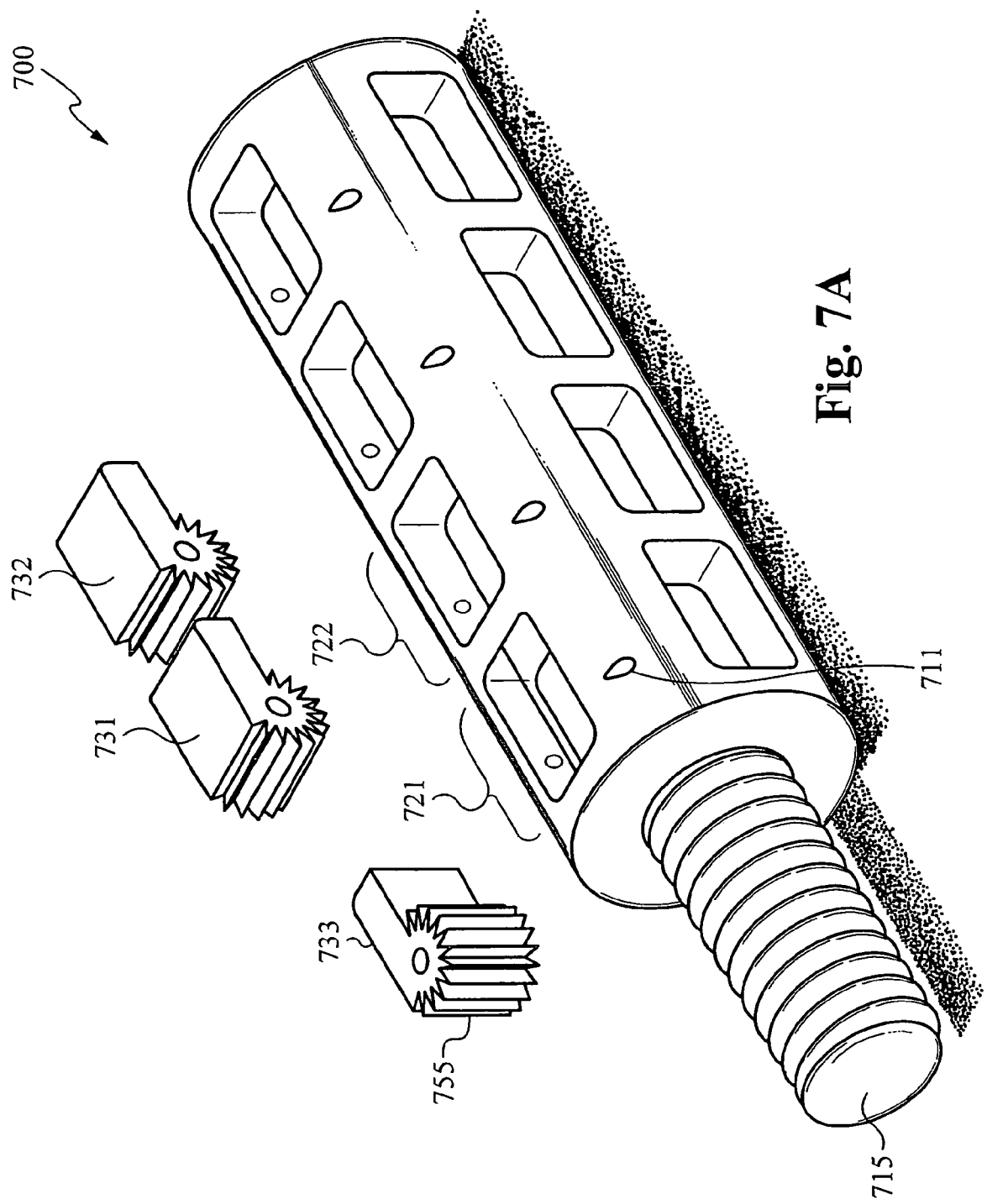
FIGS. 7A-B are perspective drawings illustrating the tabs and tab bays of some embodiments.
Figure 7B:
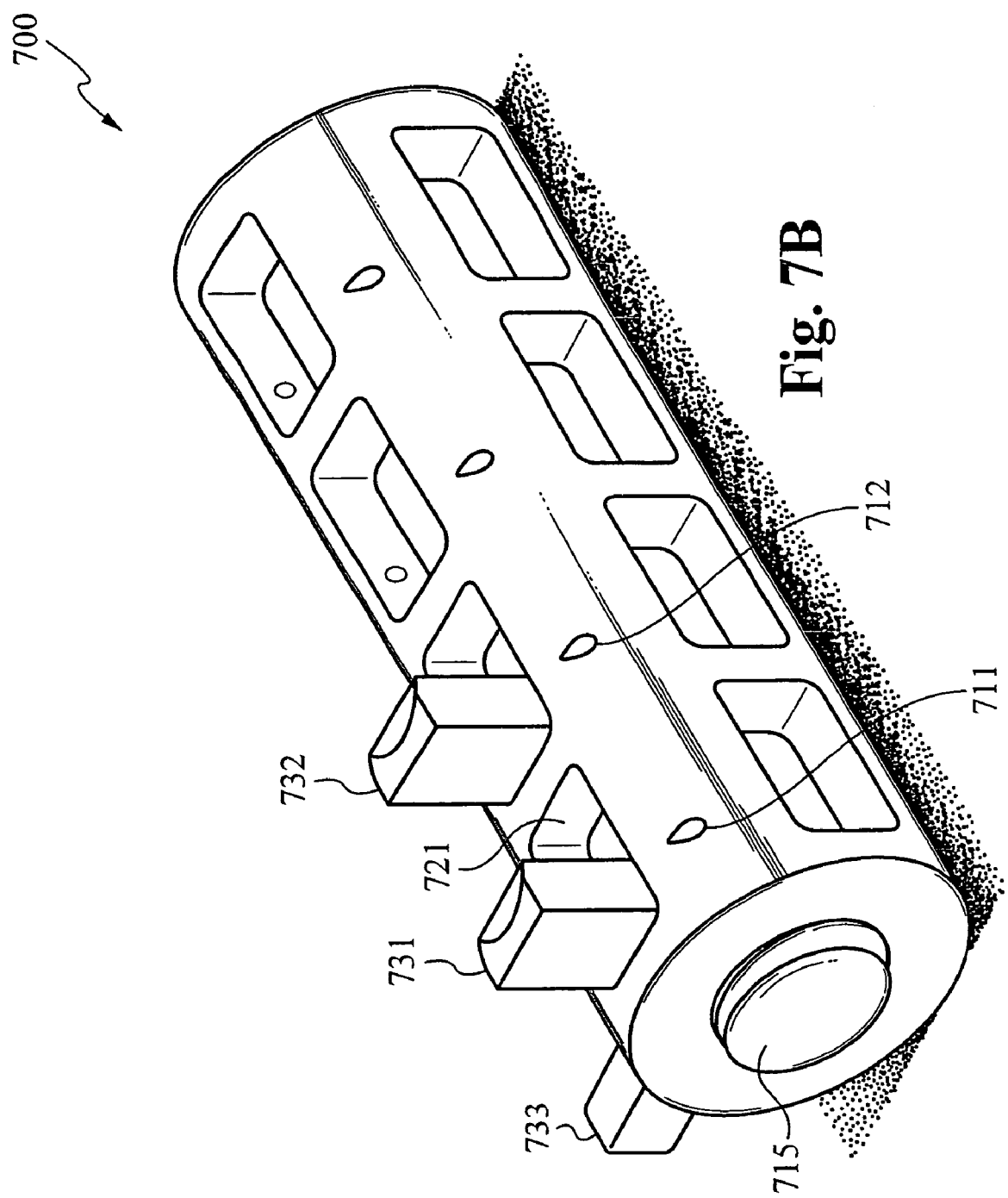

FIG. 7A is a perspective drawing illustrating the bone fusion device 700 with four tab bays on four opposite sides of the device 700, according to some embodiments of the invention. As described above, a tab is deposed in each tab bay and secured by a rotating means. For instance, the tab 731 is deposed in the tab bay 721 and secured by the rotating means 711. Also shown in FIG. 7A, a lead screw 715 is driven into the cavity. As described above, the lead screw 715 provides the thread by which the gear teeth 755 elevate the tabs 731-733. Accordingly, FIG. 7B illustrates the bone fusion device 700 with the tabs 731-733 elevated.

Figure 8:
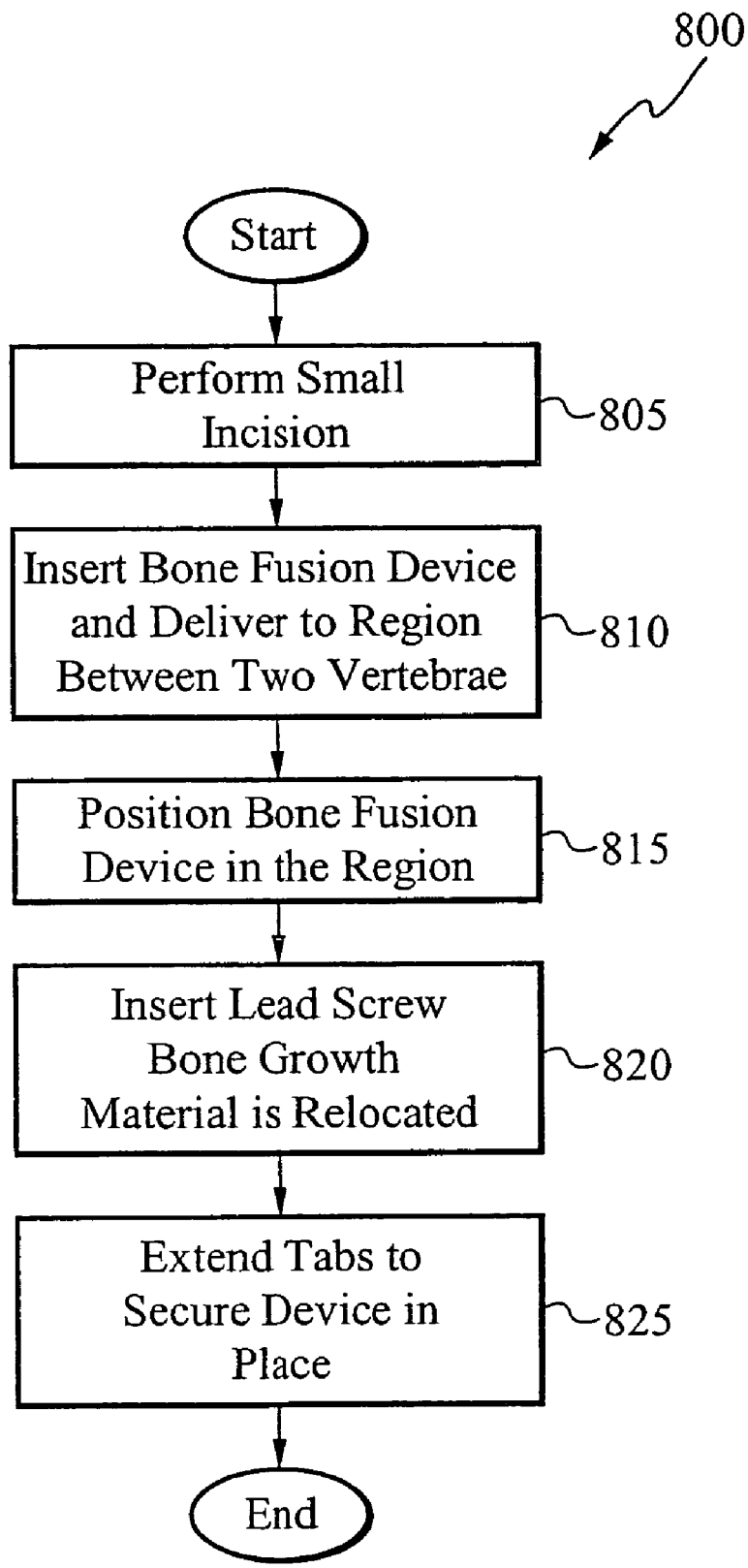
FIG. 8 illustrates a process flow in accordance with some embodiments of the invention.

FIG. 8 is a process flow diagram that summarizes the insertion and use of the bone fusion device according to some embodiments. As shown in this figure, the process 800 begins at the step 805 where a small, minimally invasive surgical incision is performed. The small incision is typically only large enough to permit entry of an arthroscopic surgical tool. Then, the process 800 transitions to the step 810, where the bone fusion device is inserted through the small incision and delivered to a region between two vertebrae that are to be fused together. Insertion and delivery of the bone fusion device are performed by using arthroscopic tool(s).

At the step 815, the bone fusion device is positioned in the region where bone fusion is to occur, also typically by using one or more arthroscopic tool(s). Once the bone fusion device is positioned in the region between the two vertebrae, the process 800 transitions to the step 820, where the lead screw is inserted and driven into the bone fusion device. The lead screw is typically driven into a cavity in the center of the bone fusion device. The cavity contains a bone growth material comprising collagen and/or a matrix for the promotion of bone growth. Accordingly, insertion of the lead screw into the cavity causes the bone growth material to be relocated from the interior cavity to the exterior surface of the bone growth device. The bone fusion device of some embodiments has a particular pattern of conduits or pores that extend from the interior cavity to the exterior surface for facilitating the relocation of bone growth material to particular locations at the exterior of the device. For instance, some embodiments have pores that facilitate the relocation of bone growth material to particular tabs.

At the step 825 of the FIG. 8, the tabs are selectively extended to lock the bone fusion device in place in the region between the two vertebrae. The tabs of some embodiments are extended by using the worm screw drive mechanism described above in relation to FIG. 4. Once the selected tabs are extended and the bone fusion device is secured in place at the step 825, the surgical tools are removed from the patient, and the small incision is sutured. Then, the process 800 concludes.

Figure 9:
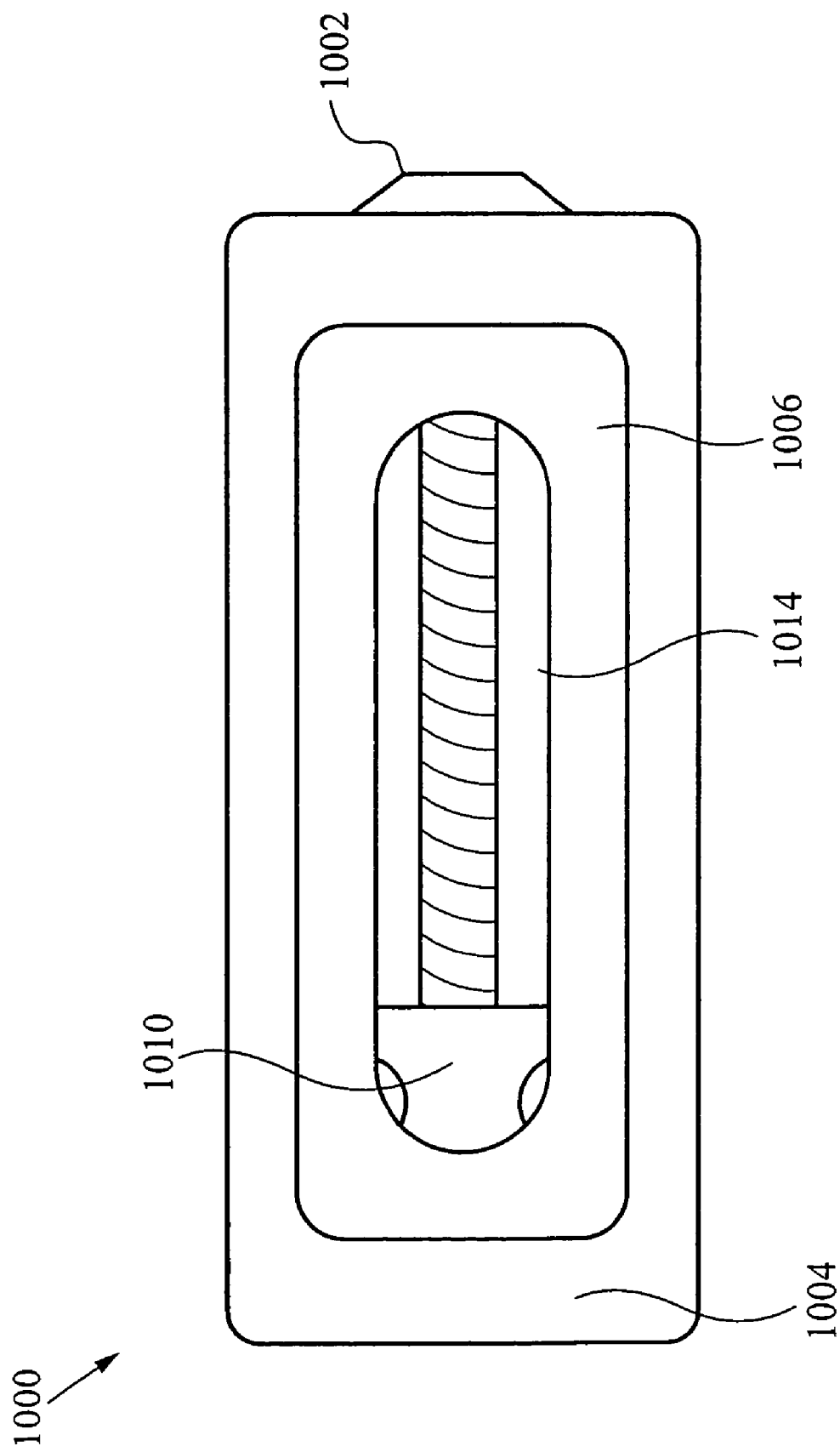
FIG. 9 illustrates a top perspective view of the bone fusion device in some embodiments of the invention.

FIG. 9 illustrates a top perspective view of the bone fusion device in some embodiments. As shown in this figure, the bone fusion device 1000 has a substantially rectangular shape and has two end faces. In some embodiments, the bone fusion device 1000 is constructed from a high strength biocompatible material, such as titanium, which has the strength to withstand compressive and shear forces in the spine that are generated by a patient's body weight and daily movements. The base biocompatible material is often textured or coated with a porous material conducive to the growth of new bone cells on the bone fusion device 1000. As further illustrated in FIG. 9, the bone fusion device 1000 has several conduits or holes 1014 which permit the bone graft material to contact the vertebral bone after the device 1000 has been inserted between the vertebrae of the patient. The bone graft material and the surface texturing of the device 1000 encourage the growth and fusion of bone from the neighboring vertebrae. The fusion and healing process will result in the bone fusion device 1000 becoming embedded within the two adjacent vertebrae of the spine which eventually fuse together during the healing period.

As further illustrated in FIG. 9, a first tab 1006 is located on a first side and a second tab 1006 (FIG. 14A) is located on an opposing second side. These tabs 1006 are shaped so that their outer surface is substantially flush with the frame 1004 of the bone fusion device 1000 in an unextended position. Internally, the tabs 1006 have an angled inner surface. Each tab 1006 is shaped such that one end is substantially larger than the opposing smaller end, and the size of the tab in between gradually decreases while going from the larger end to the opposing smaller end. A positioning means 1002 is coupled to an extending block or nut 1010 which travels up or down the positioning means 1002 depending on which way the positioning means 1002 is turned. The positioning means 1002 is typically a screw type assembly. Turning the positioning means 1002 clockwise causes the extending block 1010 to move up the positioning means 1002 towards the head of the positioning means 1002, whereas turning the positioning means 1002 counterclockwise moves the extending block 1010 away from the head of the positioning means 1002. When the extending block 1010 is positioned away from the head of the positioning means 1002, the angled tabs 1006 are compact and are within the frame 1004 of the bone fusion device 1000. Thus, the unextended tabs 1006 of the bone fusion device 1000 provide a compact assembly that is suitable for insertion into the patient's body through an arthroscopic surgical procedure. An arthroscopic procedure is considered minimally invasive and has certain advantages over more invasive conventional surgical procedures. In an arthroscopic procedure, a smaller surgical incision is employed as compared to the size of the incision required for conventional invasive surgery. Moreover, arthroscopic procedures minimize or eliminate the need for excessive retraction of a patient's tissues such as muscles and nerves, thereby minimizing trauma and injury to the muscles and nerves and further reducing the patient's recovery time. As the positioning means 1002 is rotated causing the extending block 1010 to move closer to the head of the positioning means 1002, the extending block 1010 pushes the angled tabs 1006 outward causing the tabs 1006 to assert pressure against surrounding bones and securing the bone fusion device 1000 in place. When the extending block 1006 reaches as close to the head of the positioning means 1002 as allowed, the tabs 1006 are fully extended. Furthermore, since the extending block 1010 travels along the positioning means 1002, such as along the threads of a screw, very precise positions of the tabs 1006 are able to be achieved.

Figure 10:
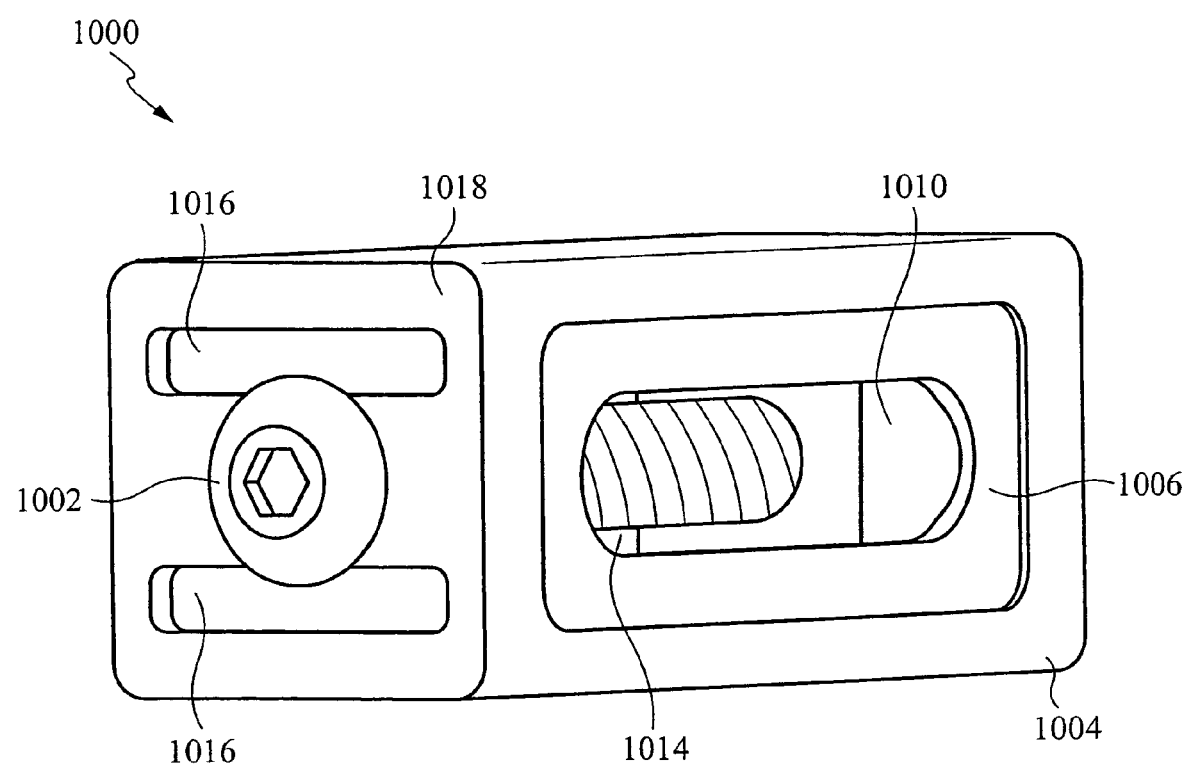
FIG. 10 illustrates a top/side perspective view of the bone fusion device in some embodiments of the invention.

FIG. 10 illustrates a top/side perspective view of the bone fusion device 1000 in some embodiments. As described above, the bone fusion device 1000 has tabs 1006 initially positioned so that they fit within the frame 1004 of the bone fusion device 1000. The positioning means 1002 is positioned through the first end face 1018 so that the extending block 1010 is able to travel along the positioning means 1002 causing the tabs 1006 to extend outwardly beyond the frame 1004 of the bone fusion device 1000. The positioning means 1002 is able to be any device that allows such functionality. Furthermore, if a screw or bolt is utilized as the positioning means 1002, any type of screw head is acceptable even though the exemplary screw slot shown in FIG. 10 requires the use of an allen wrench. Slotted, Phillips, Pozidriv, Torx, Robertson, Tri-Wing, Torq-Set, Spanner and any other heads are acceptable alternatives. Also located within the first end face 1018 are one or more apertures 1016 to allow bone graft material to contact the vertebral bone after the device 1000 has been inserted between the vertebrae of the patient. The holes 1014 within the tabs 1006 also permit the insertion of bone graft material.

Figure 11:
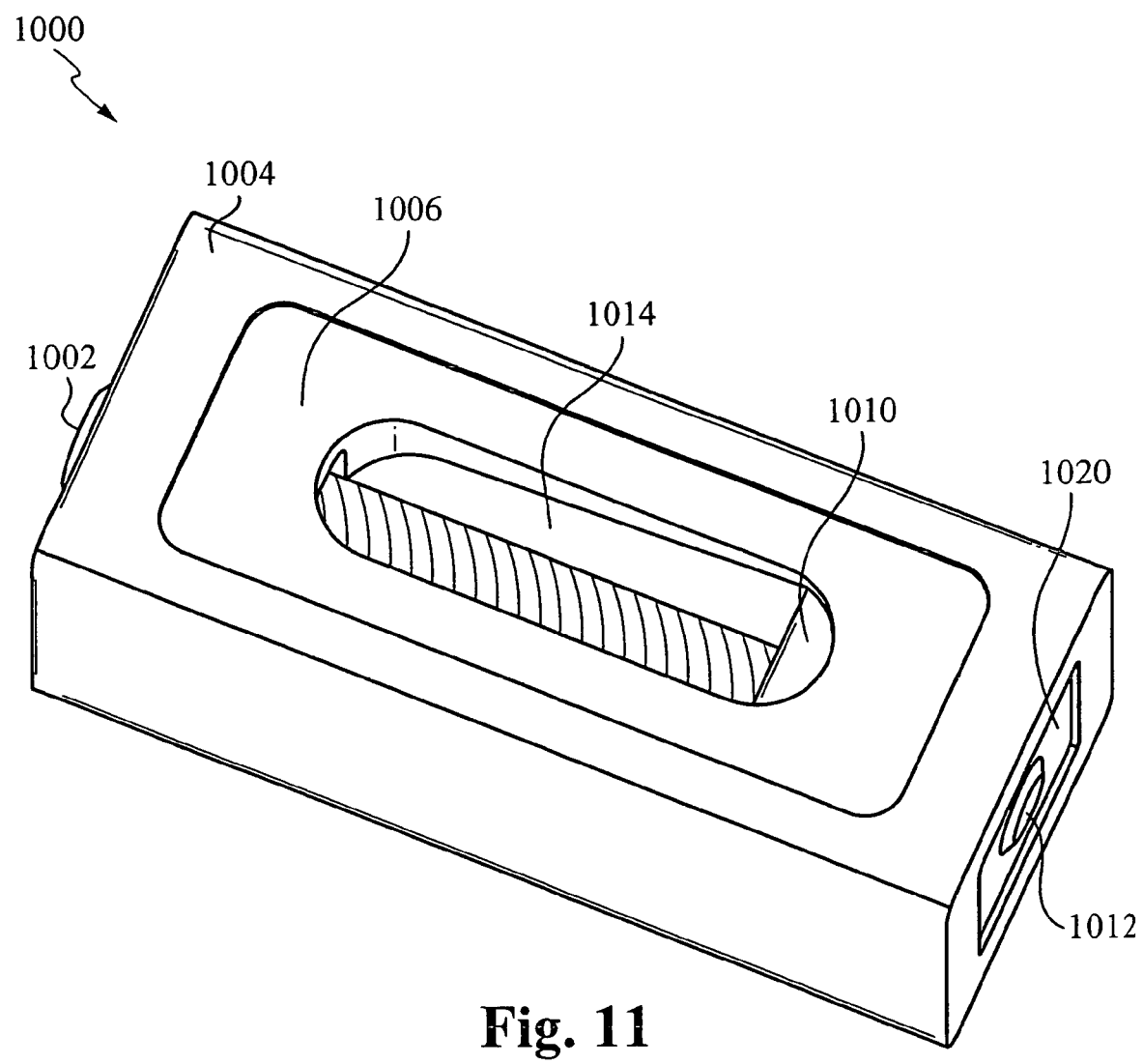
FIG. 11 illustrates a top/side perspective view of the bone fusion device in some embodiments of the invention.

FIG. 11 illustrates a top/side perspective view of the bone fusion device 1000 in some embodiments. As described before, the bone fusion device 1000 utilizes the positioning means 1002 to move the extending block 1010 up and down the body of the positioning means 1002 which forces the tabs 1006 to either extend or retract depending on the position of the extending block 1010. When the extending block 1010 is located near the head of the positioning means 1002, the extending block 1010 forces the tabs 1006 outward so that the tabs 1006 are extended beyond the frame 1000 to secure the bone fusion device 1000 in place. However, when the extending block 1010 is located away from the head of the positioning means 1002, the tabs 1006 are situated within the frame 1004, making the bone fusion device 1000 very compact. Opposing the end of the head of the positioning means is the second end face 1020 which contains an opening 1012 for providing access to a cavity within the interior of the bone fusion device 1000. In some embodiments, bone graft materials, such as the bone chips and/or the synthetic bone matrix that were mentioned above, are pre-loaded into the cavity within the bone fusion device 1000 through the opening 1012. The other holes 1014 within the tabs allow the bone graft material to contact the vertebral bone after the device 1000 has been inserted between the vertebrae of the patient.

Figure 12:
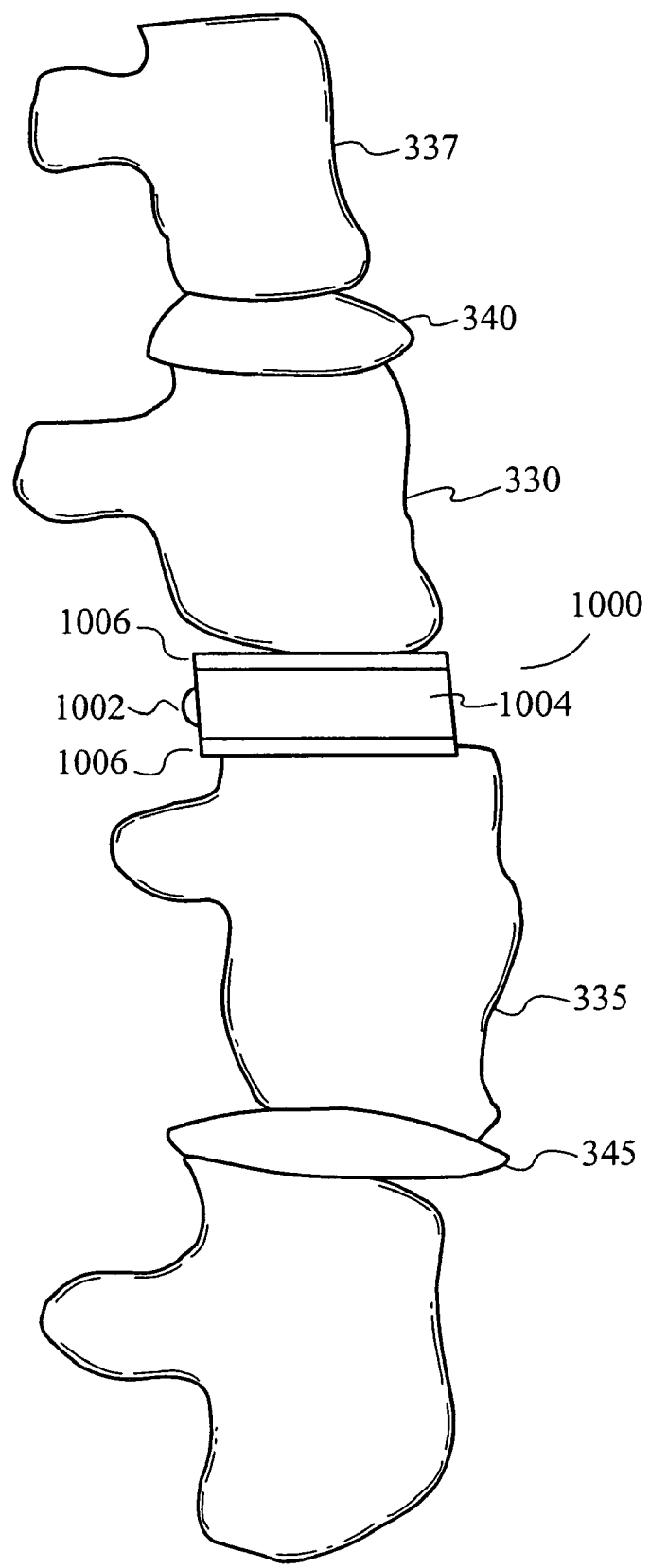
FIG. 12 illustrates a section of a vertebral column showing the bone fusion device inserted between two adjacent vertebrae in place of an intervertebral disc.

FIG. 12 illustrates a section of a vertebral column showing the bone fusion device 1000 inserted between two adjacent vertebrae 330 and 335 in place of an intervertebral disc. As shown in this figure, the bone fusion device 1000 is positioned in a location where an intervertebral disc would normally reside. A flexible disc is typically sandwiched between the two vertebrae of a normal healthy spinal column. For instance, the normal, healthy disc 340 is sandwiched between the vertebrae 337 and 330. However, for the spinal column illustrated in FIG. 12, the intervertebral disc that normally resides between the vertebrae 330 and 335 has been excised and surgical insertion of the bone fusion device 1000 has replaced the disc as the supporting structure between the vertebrae 330 and 335.

During the insertion and placement of the bone fusion device 1000, the tabs 1006 are deposed in a position aligned along the body of the bone fusion device 1000, such that the tabs lie substantially within the exterior surfaces of the device. In some embodiments, the tabs 1006 are flush with the exterior surface. In these embodiments, the form factor of the bone fusion device 1000 is configured to be as compact as possible. For example, the form factor of some embodiments has a diameter of approximately 0.28 inches and a length of approximately 1.0 inch. In contrast, the form factor of these same embodiments has a diameter of approximately 0.48 inches when the tabs 1006 are fully extended. In other embodiments the size could be larger or smaller as needed.

By minimizing the space occupied, the bone fusion device 1000 is advantageously inserted arthroscopically into the patient's body. If instead, the device 1000 were inserted in its fully extended form, a larger surgical incision would be required, and a greater displacement of the muscles and nerves would be needed. However, its compact form factor allows the bone fusion device 1000 to be inserted by advantageously utilizing minimally invasive arthroscopic techniques. Then, the tabs 1006 of the bone fusion device 1000 are extended after arthroscopic insertion to optimally increase the form factor and brace the device 1000 between the vertebrae 330 and 335.

Figure 13:
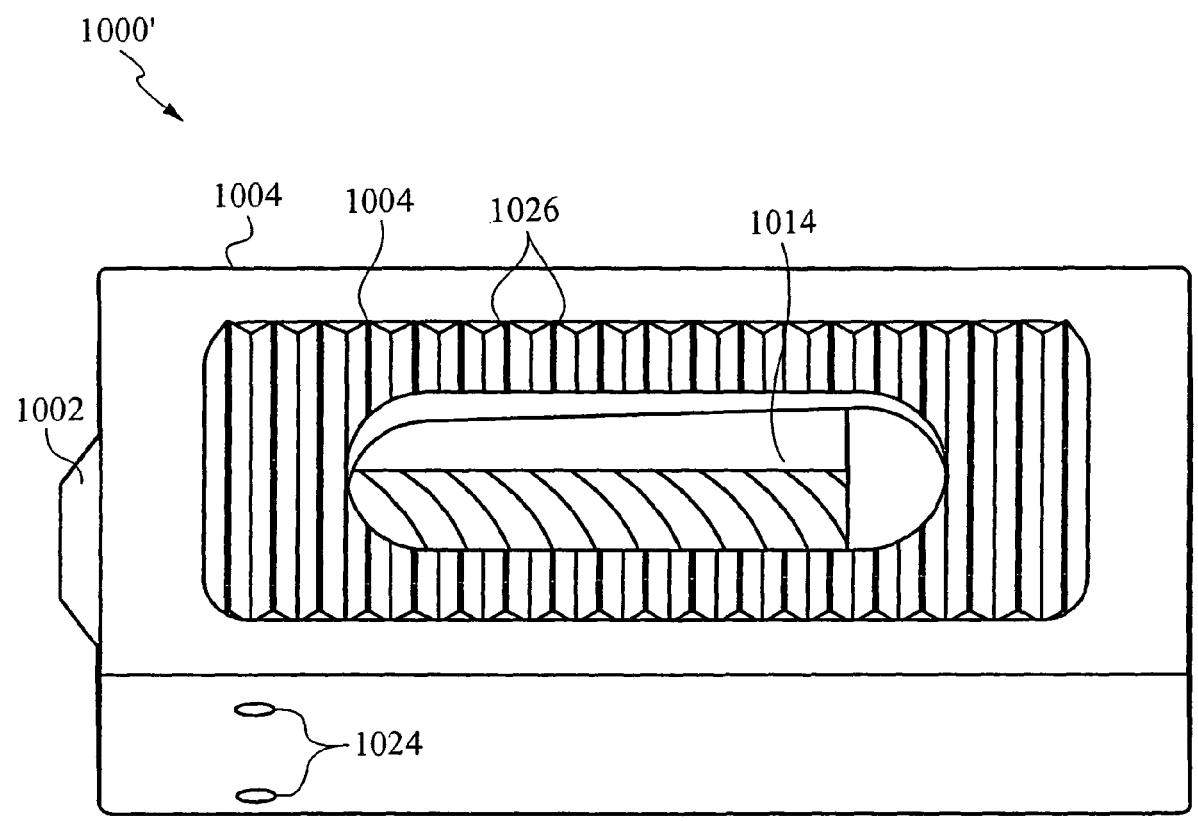
FIG. 13 illustrates a side perspective view of the bone fusion device in another embodiment of the present invention.

FIG. 13 illustrates a side view of another embodiment of the bone fusion device 1000'. The bone fusion device 1000' utilizes the positioning means 1002 to move the extending block 1010 (FIG. 9) up and down the body of the positioning means 1002 which forces the tabs 1006' to either extend or retract depending on the position of the extending block 1010 (FIG. 9). The tabs 1006' have serrated edges 1026 to further increase the bone fusion device's gripping ability to secure it in place between the bones. When the extending block 1010 (FIG. 9) is located near the head of the positioning means 1002, the extending block 1010 (FIG. 9) forces the tabs 1006' outward so that the tabs 1006' are extended beyond the frame 1000 to secure the bone fusion device 1000 in place. The tabs 1006' are each coupled to the frame 1004 of the bone fusion device 1000' by one or more slots 1028 and one or more pins 1024 wherein the one or more pins 1024 fit within the one or more slots 1028 and are able to travel along the interior of the one or more slots 1028. When the extending block 1010 (FIG. 9) is located away from the head of the positioning means 1002, the tabs 1006' are situated within the frame 1004, making the bone fusion device 1000' very compact. The holes 1014 within the tabs allow the bone graft material to contact the vertebral bone after the device 1000' has been inserted between the vertebrae of the patient.

Figure 14A:
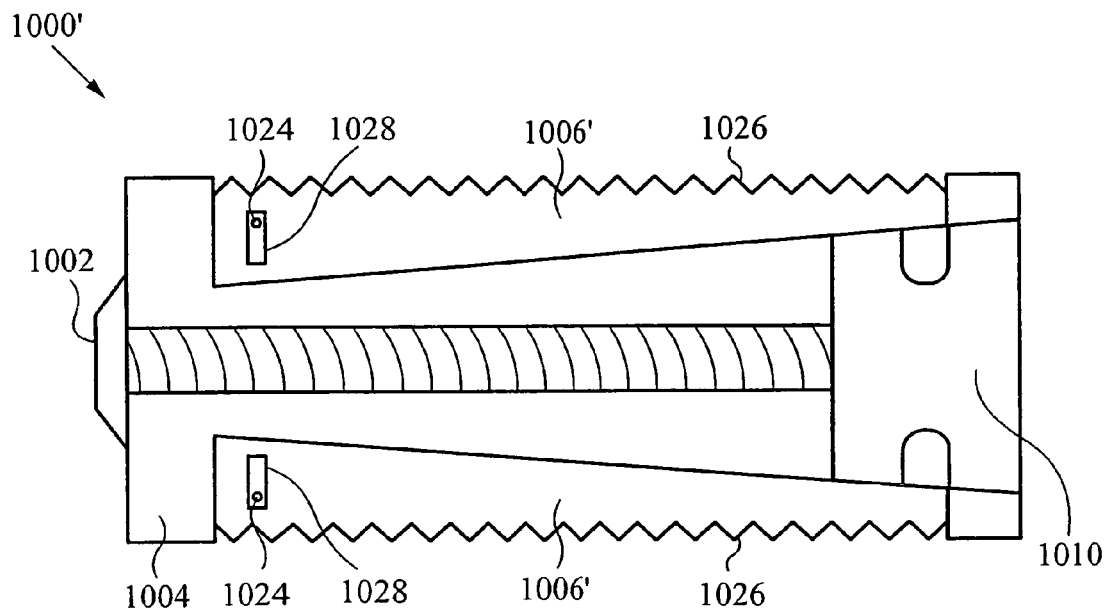
FIG. 14A illustrates a cross sectional view of the bone fusion device with the tabs compacted in another embodiment of the invention.

FIG. 14A illustrates a cross sectional view of the bone fusion device 1000' with the tabs 1006' with serrated edges 1026 compacted in another embodiment. When the extending block 1010 is positioned away from the head of the positioning means 1002 and close to the second end face 1020 (FIG. 11), the tabs 1006' are positioned within the frame 1004 of the bone fusion device 1000'. The tabs 1006' are coupled to the frame 1004 of the bone fusion device by the one or more slots 1028 and the one or more pins 1024 wherein the one or more pins 1024 fit within the one or more slots 1028 and are able to travel along the interior of the one or more slots 1028.

Figure 14B:
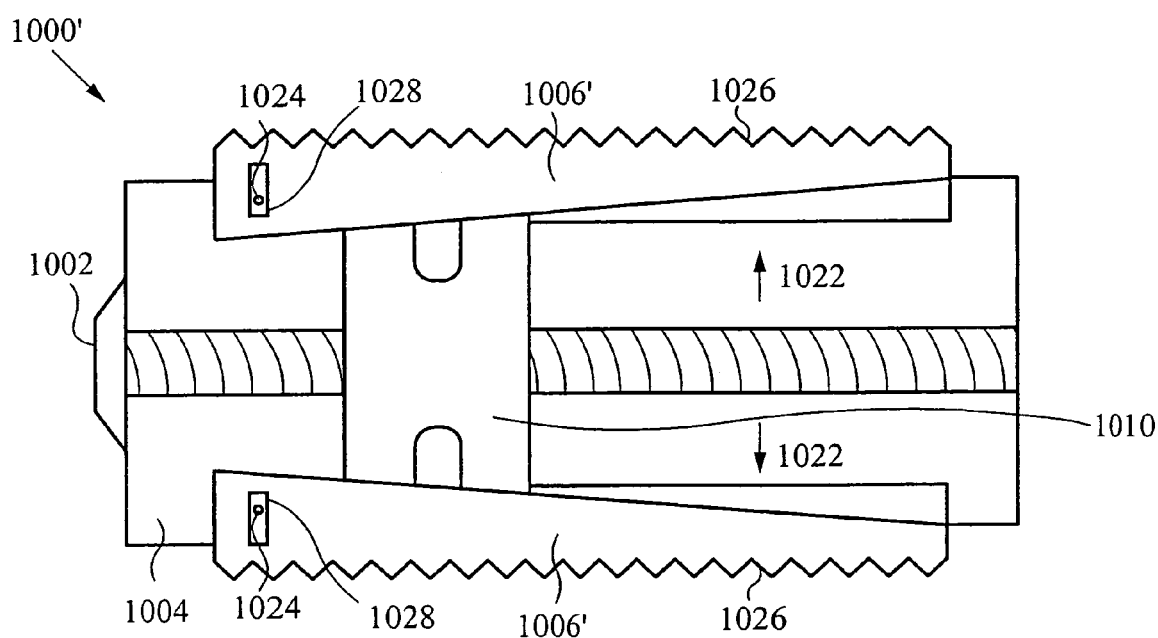
FIG. 14B illustrates a cross sectional view of the bone fusion device with the tabs extended in another embodiment of the invention.

FIG. 14B illustrates a cross sectional view of the bone fusion device 1000' with the tabs 1006' with serrated edges 1026 extended in another embodiment. When the extending block 1010 is positioned near the head of the positioning means 1002 and close to the first end face 1018 (FIG. 10), the tabs 1006' extend beyond the frame 1004 of the bone fusion device 1000' and ultimately secure the bone fusion device 1000' between two bones. The tabs 1006' extend because the extending block 1010 pushes the angled tabs 1006 outwardly as shown by the arrows 1022. The position of the extending block 1010 is changed by rotating the positioning means 1002 either clockwise or counterclockwise. The tabs 1006' are extended outward due to the force of the extending block 1010. With the tabs 1006' coupled to the frame 1004 of the bone fusion device by the one or more slots 1028 and the one or more pins 1024, the tabs 1006' are able to extend beyond the frame of the bone fusion device 1000' as the one or more pins 1024 travel within the interior of the one or more slots 1028.

Alternatively, the bone fusion device includes one or more pivots or any other rotating means that allows movement of the tabs wherein the one or more pivots are located at either end of the tabs.

To utilize the bone fusion device is some embodiments, it is initially configured in a compact position such that the extending block is located away from the head of the positioning means and towards the second end face thereby allowing the tabs to rest within the frame of the bone fusion device. The compact bone fusion device is then inserted into position within the patient. The surgeon is able to then the expand the bone fusion device by rotating the positioning means which moves the extending block towards the head of the positioning means and the first end face. As the extending block moves closer to the first end face, the tabs are pushed outwardly from the pressure of the extending block against the angled tabs. Eventually the extending block moves close enough to the first end face causing enough pressure between the extended tabs and the bones to be fused. At that point the bone fusion device is able to remain in place. Thereafter, material for fusing the bones together is inserted through the holes and openings within the bone fusion device.

Figure 15:
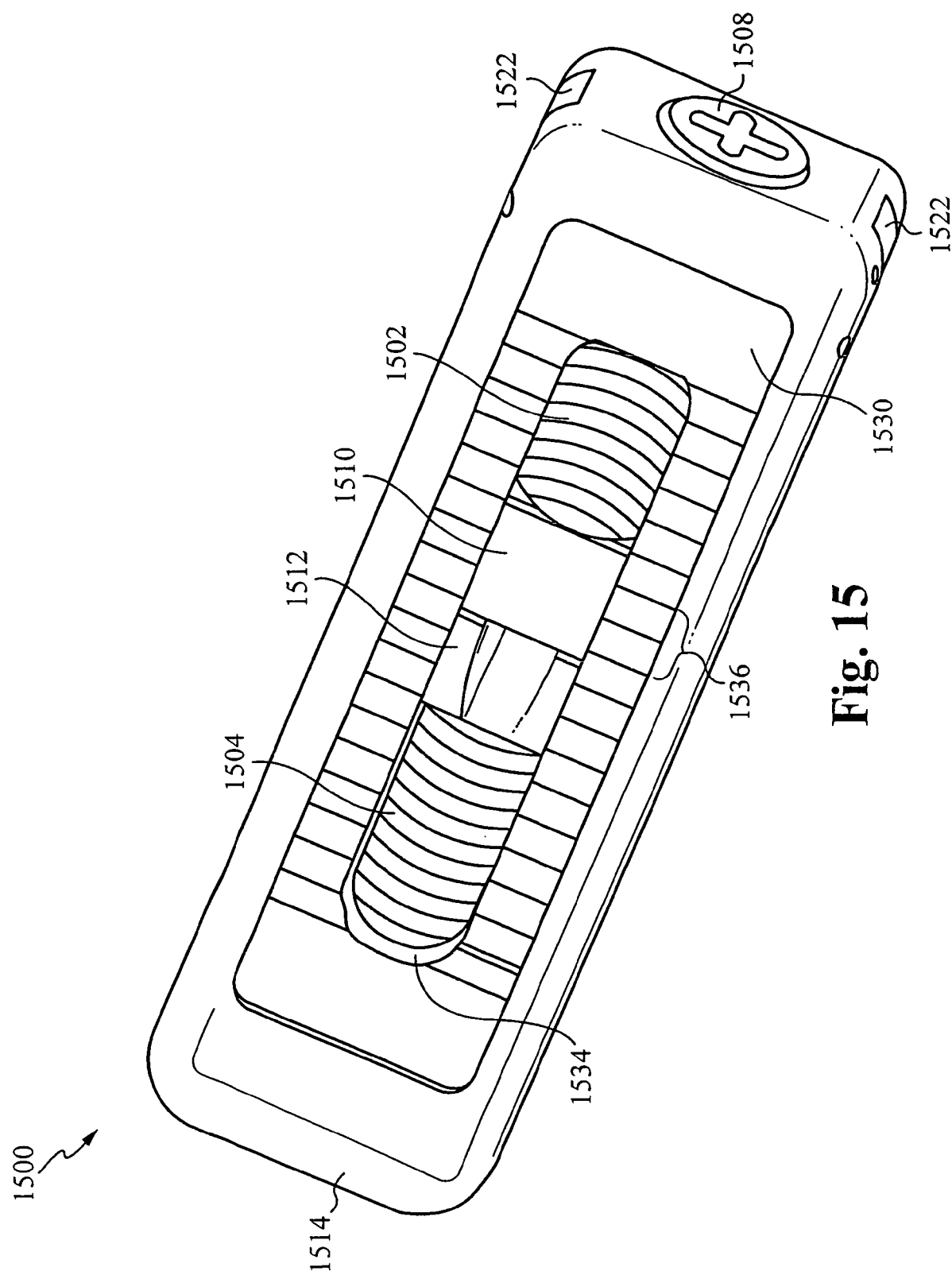
FIG. 15 illustrates a top perspective view of the bone fusion device in the preferred embodiment of the invention.

FIG. 15 illustrates a top perspective view of the bone fusion device in the preferred embodiment of the invention. As shown in this figure, the bone fusion device 1500 has a substantially rectangular shape and has two end faces. The bone fusion device 1500 is preferably constructed from a high strength biocompatible material, such as titanium, which has the strength to withstand compressive and shear forces in the spine that are generated by a patient's body weight and daily movements. The base biocompatible material is often textured or coated with a porous material conducive to the growth of new bone cells on the bone fusion device 1500. The bone fusion device 1500 has several conduits or holes 1520 (FIG. 16) and 1534 which permit the bone graft material to contact the vertebral bone after the device 1500 has been inserted between the vertebrae of the patient. The bone graft material and the surface texturing of the device 1500 encourage the growth and fusion of bone from the neighboring vertebrae. The fusion and healing process will result in the bone fusion device 1500 becoming embedded within the two adjacent vertebrae of the spine which eventually fuse together during the healing period.

As further illustrated in FIG. 15, tabs 1530 are located on opposing sides of the bone fusion device 1500. The tabs 1530 are shaped so that their outer surface is substantially flush with the frame 1514 of the bone fusion device 1500 in a nonextended position. Internally, the tabs 1530 have an angled inner surface. Each tab 1530 is shaped such that the ends are larger than the middle, and the size of the tab 1530 gradually increases while going from the middle to the ends. A positioning means 1508 within the frame 1514 of the bone fusion device 1500 comprises a first screw 1502 and a second screw 1504 coupled together. The first screw 1502 is threaded opposite of the second screw 1504. For example, if the first screw 1502 is left threaded, the second screw 1504 is right threaded or visa versa. Furthermore, the first screw 1502 is of a slightly different size than the second screw 1504. The positioning means 1508 is coupled to a first extending block 1510 and a second extending block 1512. Specifically the first extending block 1510 is coupled to the first screw 1502 and the second extending block 1512 is coupled to the second screw 1504. The first extending block 1510 and the second extending block 1512 are positioned in the middle of the bone fusion device 1500 in the compact position. When the positioning means 1508 is turned appropriately, the extending blocks 1510 and 1512 each travel outwardly on their respective screws 1502 and 1504. As the extending blocks 1510 and 1512 travel outwardly, they push the tabs 1530 outward. To retract the tabs 1530, the positioning device 1508 is turned in the opposite direction and the extending blocks 1510 and 1512 will each travel back to the middle on their respective screws 1502 and 1504. When the extending blocks 1510 and 1512 are positioned in the middle of the bone fusion device 1500, the tabs 1530 are compact and are within the frame 1514 of the bone fusion device 1500. Thus, the nonextended tabs 1530 of the bone fusion device 1500 provide a compact assembly that is suitable for insertion into the patient's body through an arthroscopic surgical procedure. An arthroscopic procedure is considered minimally invasive and has certain advantages over more invasive conventional surgical procedures. In an arthroscopic procedure, a smaller surgical incision is employed as compared to the size of the incision required for conventional invasive surgery. Moreover, arthroscopic procedures minimize or eliminate the need for excessive retraction of a patient's tissues such as muscles and nerves, thereby minimizing trauma and injury to the muscles and nerves and further reducing the patient's recovery time.

As the positioning means 1508 is rotated causing the extending blocks 1510 and 1512 to move closer to the ends of the respective screws 1502 and 1504, the extending blocks 1510 and 1512 push the tabs 1530 outward causing the tabs 1530 to assert pressure against surrounding bones and securing the bone fusion device 1500 in place. When the extending blocks 1510 and 1512 reach as close to the head of the positioning means 1508 as allowed, the tabs 1530 are fully extended. Furthermore, since the extending blocks 1510 and 1512 travel along the positioning means 1508, along the threads of the screws 1502 and 1504, very precise positions of the tabs 1530 are able to be achieved. The tabs 1530 have serrated edges 1536 to further increase the bone fusion device's gripping ability to secure it in place between the bones.

To secure the bone fusion device 1500 in place, a user generally utilizes an implement such as a screw driver to turn the positioning means 1508. Screw drivers unfortunately have the ability to slip out of place. When performing surgery near someone's spine, it is preferable to prevent or at least minimize the slipping ability. To do so, channels 1522 are implemented to receive a tool (not shown). The tool (not shown) has attachments that fit within the channels 1522 to secure the tool (not shown) in place.

Figure 16:
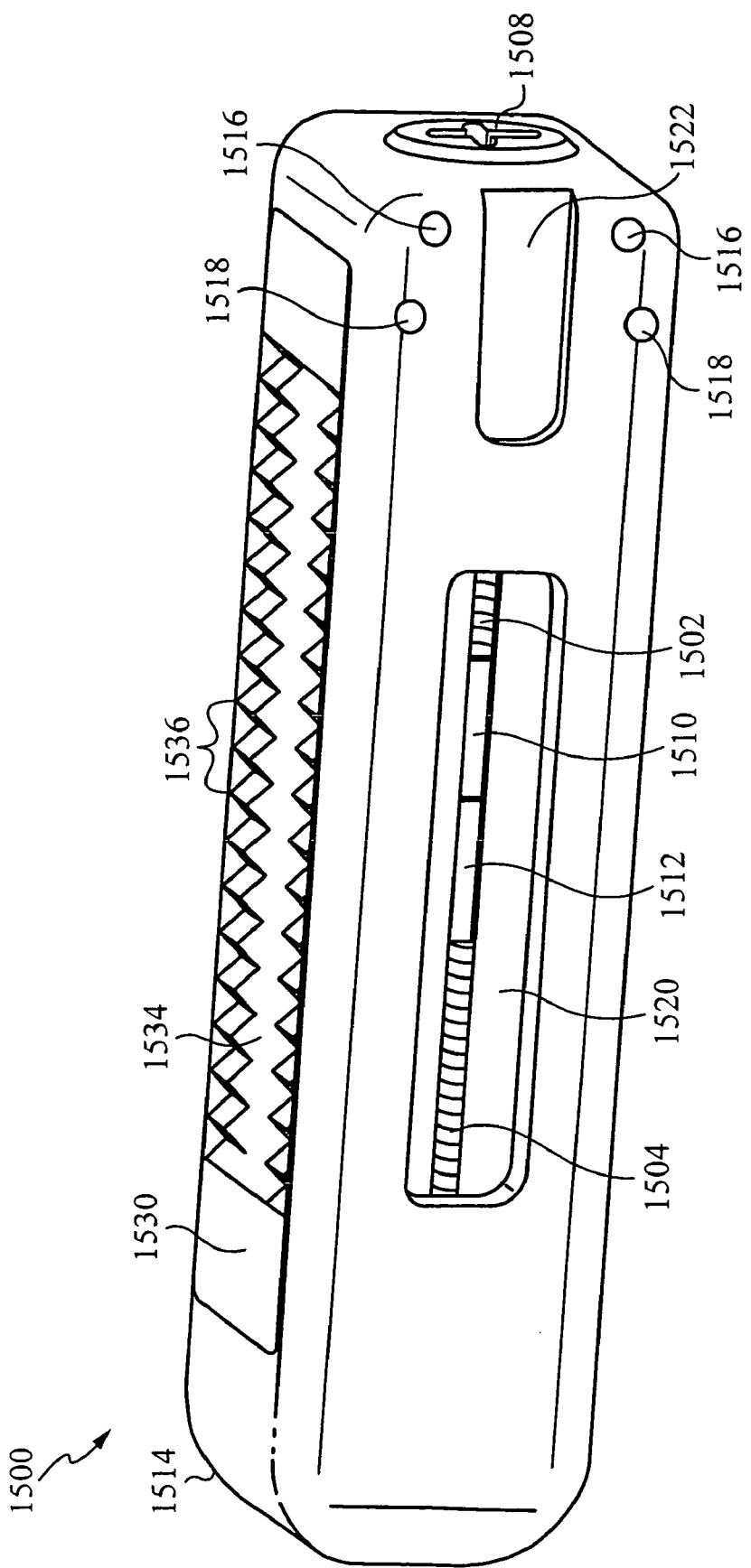
FIG. 16 illustrates a side perspective view of the bone fusion device in the preferred embodiment of the present invention.

FIG. 16 illustrates a side perspective view of the bone fusion device in the preferred embodiment of the present invention. The bone fusion device 1500 utilizes the positioning means 1508 comprising the first screw 1502 and the second screw 1504 to move the first extending block 1510 and the second extending block 1512 outwardly from the middle of the bone fusion device 1500 towards its ends. The positioning means 1508 is held in place but permitted to turn utilizing one or more first pins 1516. The one or more first pins 1516 are secured within a retaining groove 1506 (FIG. 17) of the positioning means 1508. The extending blocks 1510 and 1512 force the tabs 1530 to either extend or retract depending on where the extending blocks 1510 and 1512 are positioned. As described above, the tabs 1530 have serrated edges 1536 to further increase gripping ability. The tabs 1530 are each coupled to the frame 1514 of the bone fusion device 1500 by one or more slots 1532 (FIG. 18A) and one or more second pins 1518 wherein the one or more second pins 1518 fit within the one or more slots 1532 and are able to travel along the interior of the one or more slots 1532. The holes 1534 within the tabs 1530 allow the bone graft material to contact the vertebral bone after the device 1500 has been inserted between the vertebrae of the patient. A set of holes 1520 within the frame 1514 also allow bone graft material to be inserted within the bone fusion device 1500 afer the bone fusion device 1500 has been placed. The channels 1522 implemented to receive a tool are shown as well.

Figure 17:
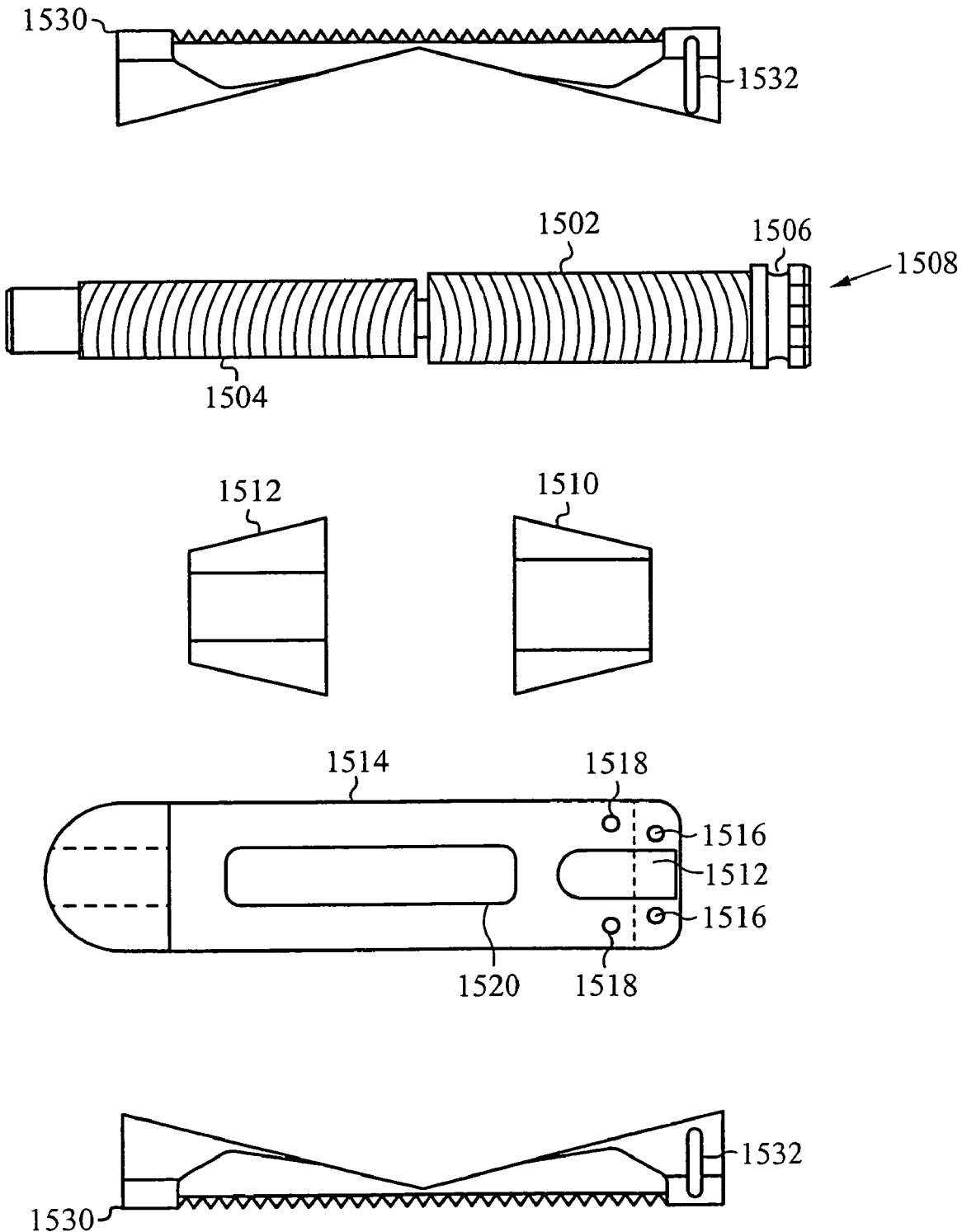
FIG. 17 illustrates a cross-sectional view of components of the bone fusion device in the preferred embodiment of the present invention.

FIG. 17 illustrates a cross-sectional view of components of the bone fusion device in the preferred embodiment of the present invention. As described above, the positioning means 1508 comprises a first screw 1502 and a second screw 1504 wherein the first screw 1502 is threaded differently than that of the second screw 1504. Furthermore, the first screw 1502 is of a slightly different size than the second screw 1504. For example, the first screw 1502 is an 8-32 screw and the second screw is a 6-32 screw. A retaining groove 1506 is utilized to secure the positioning means 1508 in place. To ensure that a device (not shown) does not slip while turning the positioning means 1508, channels 1522 are utilized to secure the device. A first extending block 1510 and a second extending block 1512 are utilized with the positioning means 1508 to extend and compact a plurality of tabs 1530. The first extending block 1510 has an internal opening to fit around the first screw 1502. The second extending block 1512 has an internal opening to fit around the second screw 1504. The frame 1514 of the bone fusion device 1500 contains a set of holes 1520 within the frame 1514 for allowing bone graft material to be inserted. Furthermore, one or more first pins 1516 secure the positioning means within the frame 1514. One or more second pins 1516 in conjunction with one or more slots 1532 secure the tabs 1530 to the frame 1514.

Figure 18A:
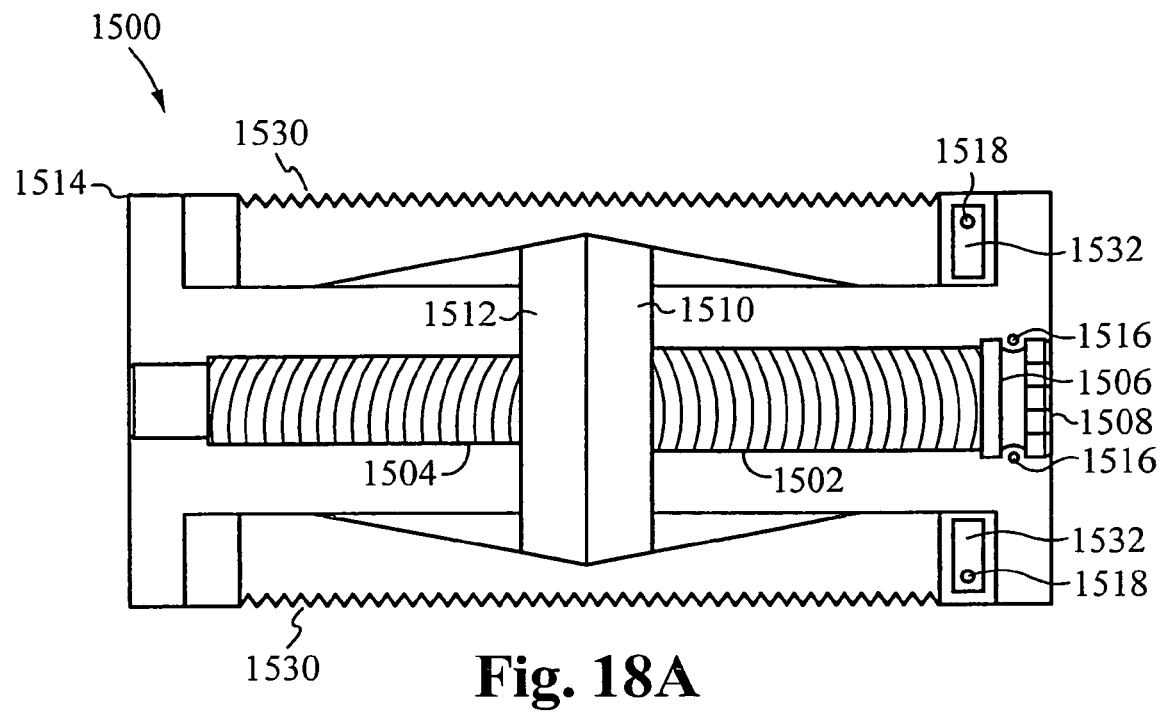
FIG. 18A illustrates a cross sectional view of the bone fusion device with the tabs compacted in the preferred embodiment of the invention.

FIG. 18A illustrates a cross sectional view of the bone fusion device with the tabs compacted in the preferred embodiment of the invention. When the extending blocks 1510 and 1512 are positioned in the middle of the positioning means 1508 with the first screw 1502 and the second screw 1504, the tabs 1530 are positioned within the frame 1514 of the bone fusion device 1500. The positioning means 1508 contains a retaining groove 1506 for holding the positioning means 1508 in place with one or more first pins 1516. The tabs 1530 are coupled to the frame 1514 of the bone fusion device 1500 using the one or more slots 1532 and the one or more second pins 1518 wherein the one or more second pins 1518 fit within the one or more slots 1532 and are able to travel along the interior of the one or more slots 1532.

Figure 18B:
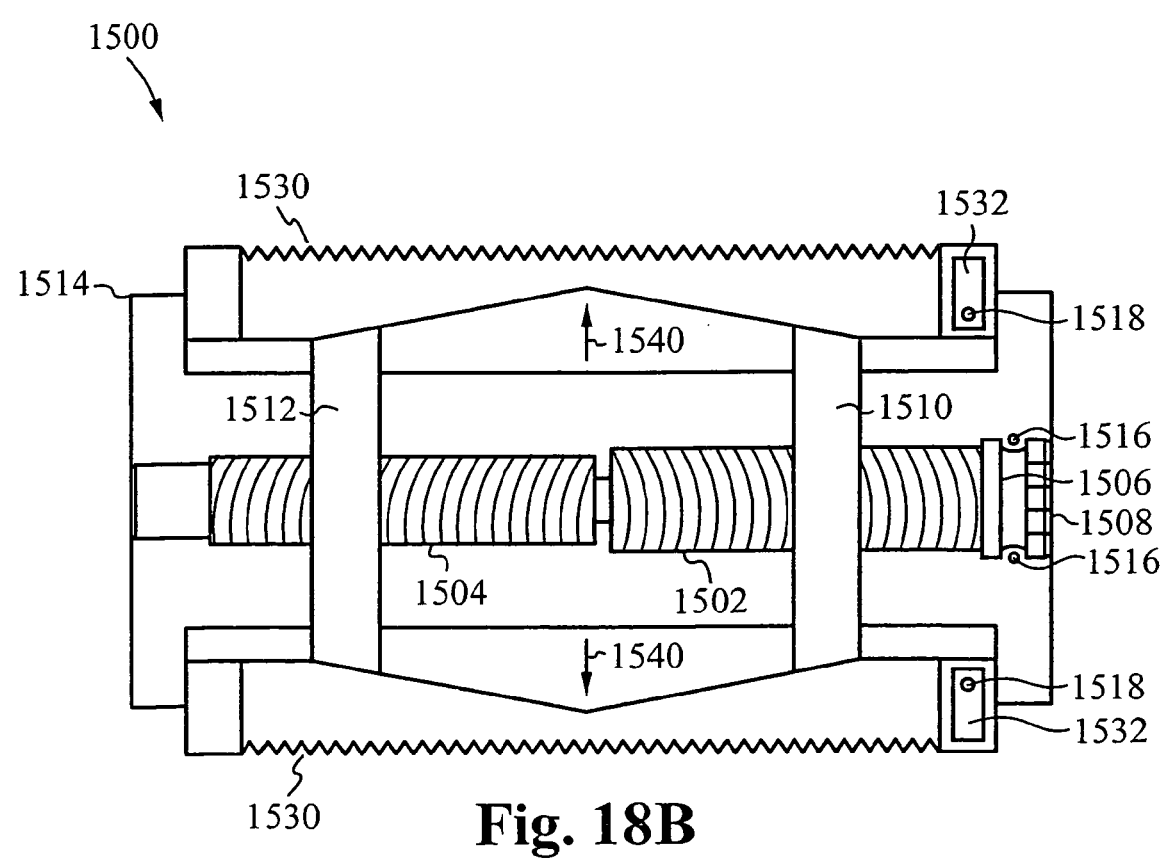
FIG. 18B illustrates a cross sectional view of the bone fusion device with the tabs extended in the preferred embodiment of the invention.

FIG. 18B illustrates a cross sectional view of the bone fusion device with the tabs extended in the preferred embodiment of the invention. As shown in FIG. 18A, the bone fusion device 1500 is compressed when the extending blocks 1510 and 1512 are in the middle of the bone fusion device 1500. As a user turns the positioning means 1508, the extending blocks 1510 and 1512 gradually move outward from the middle. If the user turns the positioning means 1508 in the opposite direction, the extending blocks move back towards the middle. As the extending blocks 1510 and 1512 are moving outward, they push on the tabs 1530. The tabs 1530 extend because the extending blocks 1510 and 1512 exert force the angled tabs 1530 outwardly as shown by the arrows 1540. When the extending blocks 1510 and 1512 are positioned near the ends of the bone fusion device 1500, the tabs 1530 extend beyond the frame 1514 of the bone fusion device 1500 and ultimately secure the bone fusion device 1500 between two bones. With the tabs 1530 coupled to the frame 1514 of the bone fusion device 1500 by the one or more slots 1532 and the one or more second pins 1518, the tabs 1530 are able to extend beyond the frame 1514 of the bone fusion device 1500 as the one or more second pins 1518 travel within the interior of the one or more slots 1532.

To utilize the bone fusion device in the preferred embodiment, it is initially configured in a compact position such that the extending blocks are located in the middle of the bone fusion device thereby allowing the tabs to rest within the frame of the bone fusion device. The compact bone fusion device is then inserted into position within the patient. The surgeon is able to then the expand the bone fusion device by rotating the positioning means which moves the extending blocks towards the opposing ends of the bone fusion device—one near the head of the positioning means and the other towards the tail of the positioning means. As the extending blocks move away from the middle, the tabs are pushed outwardly from the pressure of the extending block against the angled tabs. Eventually the extending blocks exert a satisfactory force between the extended tabs and the bones to be fused. At that point the bone fusion device is able to remain in place. Thereafter, material for fusing the bones together is inserted through the holes and openings within the bone fusion device.

As mentioned above, the small incision and minimally invasive (arthroscopic) surgical procedure advantageously promote health and rapid recovery by the patient. Preferably, bone growth occurs around the bone fusion device and particularly at the locations of the extended tabs, such that the bone fusion device is further secured by the bone growth, which further promotes a superior, robust bone fusion result.

The present invention has been described in terms of specific embodiments incorporating details to facilitate the understanding of principles of construction and operation of the invention. Such reference herein to specific embodiments and details thereof is not intended to limit the scope of the claims appended hereto. It will be apparent to those skilled in the art that modification may be made in the embodiments chosen for illustration without departing from the spirit and scope of the invention.

What is claimed is:

1. A bone fusion device for insertion between bones comprising:
   a. a body comprising first and second ends and an exterior surface having one or more channels;
   b. an interior cavity deposed between the first and second ends;
   c. a conduit providing a pathway from the interior cavity to the exterior surface;
   d. one or more tabs for bracing the bone fusion device in a space between the bones, each tab comprising a first tab end proximate the first end and a second tab end distal from the first end and proximate the second end;
   e. a positioning element positioned through the first end and substantially within the interior cavity having an aperture configured to permit an engaging member of a tool to rotate the positioning element; and
   f. a plurality of extending blocks coupled to the positioning element and in contact with the one or more tabs for moving the one or more tabs, wherein as the positioning element moves the plurality of extending blocks from a compact position to an extended position, the tabs are raised towards an extended position with the extending blocks directly supporting the first tab end and the second tab end when in the extended position;
wherein the channels are each positioned along the exterior surface on a plane perpendicular to the aperture of the positioning element such that one or more supporting members of the tool are able to enter the one or more channels by moving along the plane thereby securing the engaging member of the tool within the aperture, and further wherein the exterior surface faces away from the interior cavity.

2. The bone fusion device as claimed in claim 1, wherein the positioning element comprises a first screw and a second screw.

3. The bone fusion device as claimed in claim 2, wherein the first screw is threaded oppositely from the second screw.

4. The bone fusion device as claimed in claim 2, wherein the first screw is larger than the second screw.

5. The bone fusion device as claimed in claim 1, wherein the one or more tabs are shaped with ends that are larger than the middle.

6. The bone fusion device as claimed in claim 1, wherein the one or more tabs contain a narrow middle section and gradually increase in size outwardly to the ends.

7. The bone fusion device as claimed in claim 1, wherein the extending blocks are nuts.

8. The bone fusion device as claimed in claim 1, wherein the plurality of extending blocks move the one or more tabs when the positioning element is rotated.

9. The bone fusion device as claimed in claim 1, further comprising serrated edges on the one or more tabs.

10. The bone fusion device as claimed in claim 1, wherein the outer surface of the tabs, for contacting the bones and that faces away from the interior cavity, has an unbroken perimeter.

11. The bone fusion device as claimed in claim 1, wherein the tabs are raised generally parallel to each other.

12. A bone fusion device for insertion between adjacent bones, comprising:
   a. a hollow body comprising a first end, a second end and one or more holes along a length of the hollow body;
   b. one or more moveable tabs each comprising a first tab end proximate the first end and a second tab end distal from the first end and proximate the second end, each tab attached to the hollow body by a pin and a slot, wherein the one or more moveable tabs are aligned along a surface of the hollow body in a compact position during insertion into a patient;
   c. a positioning element coupled through the hollow body and substantially within the hollow body having an aperture configured to permit an engaging member of a tool to rotate the positioning element; and
   d. a plurality of extending blocks coupled to the positioning element and in contact with the one or more moveable tabs for moving the one or more moveable tabs when the positioning element is rotated, wherein as the positioning element moves the plurality of extending blocks from a compact position to an extended position, the tabs are raised towards an extended position with the extending blocks directly supporting the first tab end and the second tab end when in the extended position;

wherein the surface faces away from bone fusion device and comprises one or more channels positioned along the surface of the length of the hollow body such that one or more supporting members of the tool are able to enter the one or more channels from the same direction that the engaging member of the tool enters the aperture of the positioning element in order to secure the engaging member of the tool within the aperture.

13. The bone fusion device as claimed in claim 12, wherein the positioning element comprises a first screw and a second screw.

14. The bone fusion device as claimed in claim 13, wherein the first screw is threaded oppositely from the second screw.

15. The bone fusion device as claimed in claim 13, wherein the first screw is larger than the second screw.

16. The bone fusion device as claimed in claim 12, wherein the one or more moveable tabs are shaped with ends that are larger than the middle.

17. The bone fusion device as claimed in claim 12, wherein the one or more moveable tabs contain a narrow middle section and gradually increase in size outwardly to the ends.

18. The bone fusion device as claimed in claim 12, wherein the plurality of extending blocks are nuts.

19. The bone fusion device as claimed in claim 12, further comprising serrated edges on the one or more moveable tabs.

20. A bone fusion device for insertion between adjacent bones, comprising:
   a. a hollow body comprising a first end, a second end and one or more holes along a length of the hollow body;
   b. one or more moveable tabs each comprising a first tab end proximate the first end and a second tab end distal from the first end and proximate the second end, each tab attached to the hollow body by a pin and a slot, wherein the one or more moveable tabs are aligned along a surface of the hollow body in a compact position during insertion into a patient, further wherein the first tab end and the second tab end are larger than a middle of the one or more moveable tabs such that a size of the tabs in between gradually decreases while going from the ends to the middle;
   c. a positioning element coupled through the hollow body and substantially within the hollow body, wherein the positioning element comprises a first screw, a second screw and a aperture configured to permit an engaging member of a tool to rotate the positioning element; and
   d. a plurality of extending blocks coupled to the positioning element and comprising one or more angled surfaces abutting against the one or more movable tabs for moving the one or more moveable tabs when the positioning element is rotated, wherein as the positioning element moves the plurality of extending blocks from a compact position to an extended position, the tabs are raised towards an extended position with the extending blocks directly supporting the first tab end and the second tab end when in the extended position;

wherein the surface faces away from the bone fusion device and comprises one or more channels positioned along the surface of the length of the hollow body such that one or more supporting members of the tool are able to enter the one or more channels from the same direction that the engaging member of the tool enters the aperture of the positioning element in order to secure the engaging member of the tool within the aperture.

21. The bone fusion device as claimed in claim 20, wherein the first screw is threaded oppositely from the second screw.

22. The bone fusion device as claimed in claim 20, wherein the first screw is larger than the second screw.

23. The bone fusion device as claimed in claim 20, wherein the plurality of extending blocks are nuts.

24. The bone fusion device as claimed in claim 20, further comprising serrated edges on the one or more moveable tabs.

25. A method of implanting a bone fusion device between bones, the method comprising:
   a. inserting the bone fusion device between the bones, wherein the bone fusion device comprises a first end, a second end, an internal cavity, a body having an exterior surface facing away from the internal cavity, a positioning element having an aperture configured to permit an engaging member of a tool to rotate the positioning element, and a plurality of extending blocks, one or more moveable tabs each in contact with one of the extending blocks and comprising a first tab end proximate the first end and a second tab end distal from the first end and proximate the second end, wherein the exterior surface comprises one or more channels each positioned along the surface on a plane perpendicular to the aperture of the positioning element such that one or more supporting members of the tool are able to enter the one or more channels by moving along the plane in order to secure the engaging member of the tool within the aperture;
   b. pre-configuring the one or more moveable tabs to lie within the exterior surface by using the positioning element with the plurality of extending blocks such that the bone fusion device has a minimized form factor with the plurality of extending blocks positioned in a middle of the internal cavity; and
   c. extending the one or more tabs to a desired position by moving the plurality of extending blocks away form the middle of the internal cavity towards the first end and the second end, by rotating the positioning element, wherein the extending blocks directly support the first tab end and the second tab end when the tabs are in the extended position.

26. The method as claimed in claim 25, wherein the positioning element comprises a first screw and a second screw.

27. The method as claimed in claim 26, wherein the first screw is threaded oppositely from the second screw.

28. The method as claimed in claim 26, wherein the first screw is larger than the second screw.

29. The method as claimed in claim 25, wherein the one or more tabs are shaped with ends that are larger than the middle.

30. The method as claimed in claim 25, wherein the one or more tabs contain a narrow middle section and gradually increase in size outwardly to the ends.

31. The method as claimed in claim 25, wherein rotating the positioning element clockwise moves the plurality of extending blocks, forcing the one or more moveable tabs outward.

32. The method as claimed in claim 25, wherein rotating the positioning element counterclockwise moves the plurality of extending blocks, allowing the one or more moveable tabs to move inward.

33. The method as claimed in claim 25, further comprising before implantation, depositing a bone graft material into the cavity.

34. The method as claimed in claim 25, further comprising applying bone growth material to the one or more tabs after extension, wherein the bone growth material stimulates regeneration of bone cells in the bones.

35. The method as claimed in claim 25, wherein the one or more moveable tabs further comprise serrated edges.

36. A bone fusion device for insertion between bones comprising:
 a. a first and second ends;
 b. an interior cavity deposed between the first and second ends;
 c. an exterior surface facing away from the interior cavity;
 d. a conduit providing a pathway from the interior cavity to the exterior surface;
 e. one or more tabs for bracing the bone fusion device in a space between the bones, each tab comprising a first tab end proximate the first end and a second tab end distal from the first end and proximate the second end;
 f. a positioning element positioned through the first end and substantially within the interior cavity having an aperture configured to permit an engaging member of a tool to rotate the positioning element;
 g. a plurality of extending blocks coupled to the positioning element for moving the one or more tabs, the plurality of extending blocks positioned in a middle of the interior cavity when the tabs are in a compact position, wherein the plurality of extending blocks are in contact with the tabs, such that as the positioning element moves the plurality of extending blocks away from the compact position, the tabs are raised generally parallel to each other towards an extended position, wherein the extending blocks directly support the first tab end and the second tab end when the tabs are in the extended position; and
 h. one or more channels each positioned along the exterior surface on a plane perpendicular to the aperture of the positioning element such that one or more supporting members of the tool are able to enter the one or more channels by moving along the plane in order to secure the engaging member of the tool within the aperture, wherein the positioning element is configured to rotate the independent of the one or more channels.

37. The bone fusion device as claimed in claim,36, wherein the one or more tabs contain a narrow middle section and gradually increase in size outwardly towards the first tab end and the second tab end.

* * * * *